United States Patent [19]

Briggs et al.

[11] Patent Number: 5,560,811
[45] Date of Patent: Oct. 1, 1996

[54] CAPILLARY ELECTROPHORESIS APPARATUS AND METHOD

[75] Inventors: Jonathan Briggs, Los Altos Hills; Randy M. McCormick, Santa Clara; David W. Hoyt, Saratoga, all of Calif.

[73] Assignee: Seurat Analytical Systems Incorporated, Sunnyvale, Calif.

[21] Appl. No.: 408,683

[22] Filed: Mar. 21, 1995

[51] Int. Cl.[6] .......................... B01D 57/02; B01D 59/42; C07K 1/26; C25B 7/00
[52] U.S. Cl. ........................................... 204/451; 204/601
[58] Field of Search ............................. 204/299 R, 180.1

[56] References Cited

U.S. PATENT DOCUMENTS

| | | | |
|---|---|---|---|
| 5,274,240 | 12/1993 | Mathies et al. | 204/299 R |
| 5,324,401 | 6/1994 | Yeung et al. | 204/299 R |
| 5,332,480 | 7/1994 | Datta et al. | 204/299 R |
| 5,356,525 | 10/1994 | Goodale et al. | 204/299 R |
| 5,439,578 | 8/1995 | Dovichi et al. | 204/299 R |

Primary Examiner—John Niebling
Assistant Examiner—Edna Wong
Attorney, Agent, or Firm—Banner & Allegretti, Ltd.

[57] ABSTRACT

This invention involves method and apparatus for multiplexing electrophoresis analysis. An array of samples in multi well plates are simultaneously transferred to an array of electrophoresis column where electrophoresis is simultaneously carried out followed by analysis of the columns. The methods and apparatus of this invention are, for example, useful for DNA analysis, including sequencing, and for measuring reactions between specifically binding proteins and their binding partners.

17 Claims, 16 Drawing Sheets

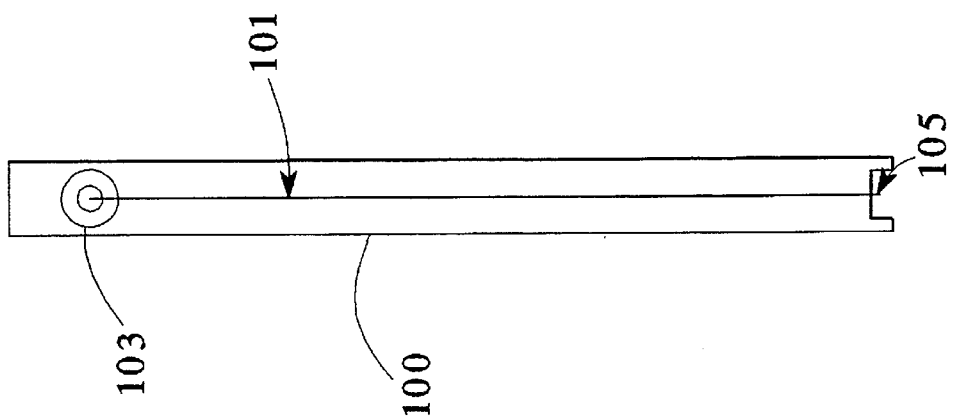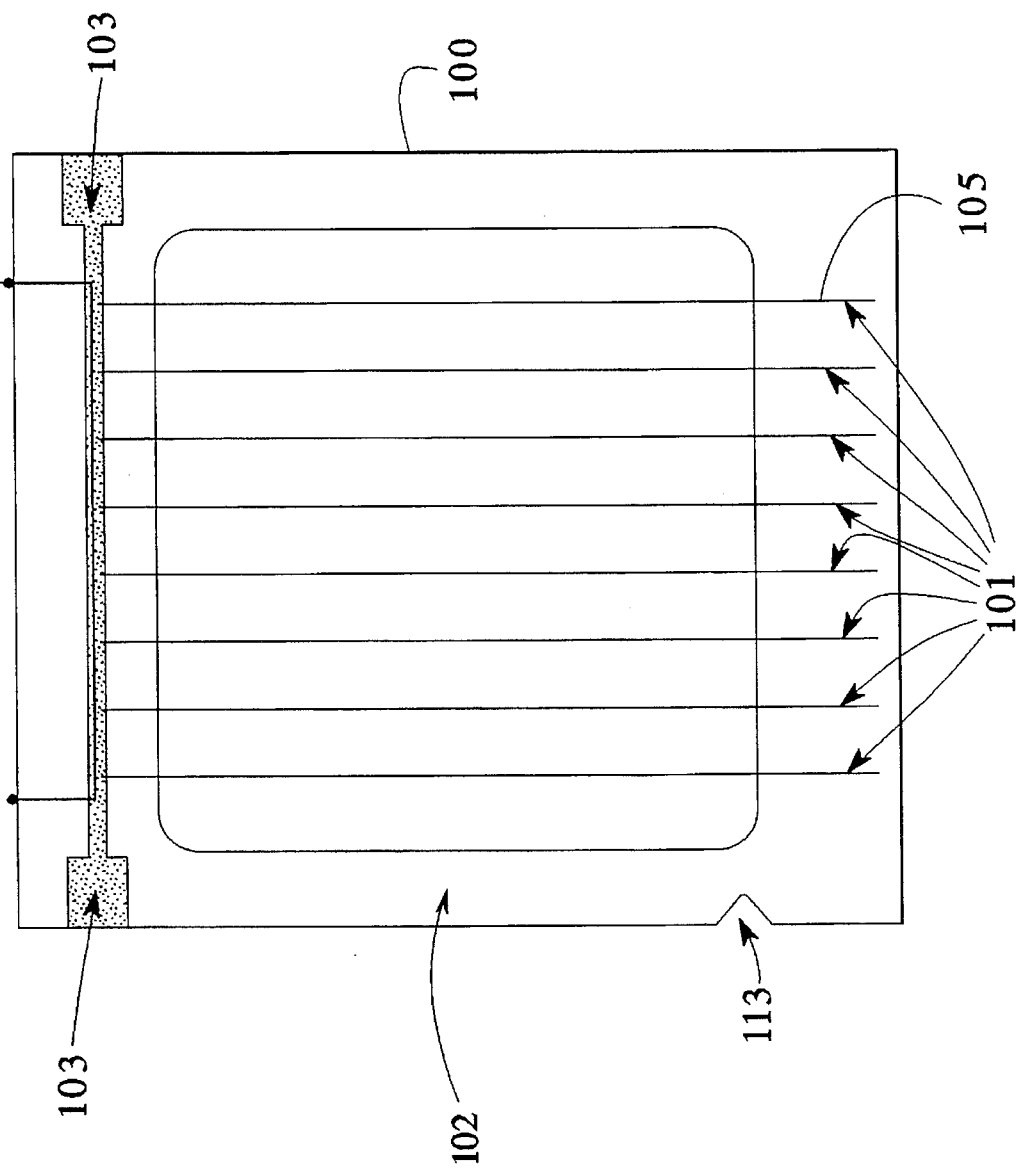

CAPILLARY ELECTROPHORESIS APPARATUS AND METHOD

BACKGROUND OF THE INVENTION

A. Field Of the Invention

This invention is in the field of separation of biomolecules and, in particular, separations by capillary electrophoresis and the use of the capillary electrophoresis to detect such molecules.

B. Background of the Prior Art

Electrophoresis is a separation process in which molecules with a net charge migrate through a medium under the influence of an electric field. Traditionally, slab gel electrophoresis has been a widely used tool in the analysis of genetic materials. See, for example, G. L. Trainor, Anal. Chem., 62, 418–426 (1990). Capillary electrophoresis has emerged as a powerful separation technique, with applicability to a wide range of molecules from simple atomic ions to large DNA fragments. In particular, capillary electrophoresis has become an attractive alternative to slab gel electrophoresis for biomolecule analysis, including DNA sequencing. See, for example, Y. Baba et at., Trends in Anal. Chem., 11, 280–287 (1992). This is generally because the small size of the capillary greatly reduces Joule heating associated with the applied electrical potential. Furthermore, capillary electrophoresis requires less sample and produces faster and better separations than slab gels.

Currently, sophisticated experiments in chemistry and biology, particularly molecular biology, involve evaluating large numbers of samples. For example, DNA sequencing of genes is time consuming and labor intensive. In the mapping of the human genome, a researcher must be able to process a large number of samples on a daily basis. If capillary electrophoresis can be conducted and monitored simultaneously on many capillaries, i.e., multiplexed, the cost and labor for such projects can be significantly reduced. Attempts have been made to sequence DNA in slab gels with multiple lanes to achieve multiplexing. However, slab gels are not readily amenable to a high degree of multiplexing and automation. Difficulties exist in preparing uniform gels over a large area, maintaining gel to gel reproducibility and loading sample wells. Furthermore, difficulties arise as a result of the large physical size of the separation medium, the requirements for uniform cooling, large amounts of media, buffer, and samples, and long run times for extended reading of nucleotide sequences. Unless capillary electrophoresis can be highly multiplexed and multiple capillaries run in parallel, the advantages of capillary electrophoresis cannot produce substantial improvement in shortening the time needed for sequencing the human genome.

Capillary electrophoresis possesses several characteristics which makes it amenable to this application. The substantial reduction of Joule heating per lane makes the overall cooling and electrical requirements more manageable. The cost of materials per lane is reduced because of the smaller sample sizes. The reduced band dimensions are ideal for excitation by laser beams, as well as focused extended sources, and for imaging onto array detectors or discrete spot detectors. The concentration of analyte into such small bands results in high sensitivity. The use of electromigration injection, i.e., applying the sample to the capillary by an electrical field, provides reproducible sample introduction with little band spreading, minimal sample consumption, and little labor.

Among the techniques used for detecting target species in capillary electrophoresis, laser-excited fluorescence detection so far has provided the lowest detection limits. Therefore, fluorescence detection has been used for the detection of a variety of analytes, especially macromolecules, in capillary electrophoresis. For example, Zare et al. (U.S. Pat. No. 4,675,300) discusses a fluoroassay method for the detection of macromolecules such as genetic materials and proteins in capillary electrophoresis. Yeung et al. (U.S. Pat. No. 5,006,210) presented a system for capillary zone electrophoresis with laser-induced indirect fluorescence detection of macromolecules, including proteins, amino acids, and genetic materials.

Systems such as these generally involve only one capillary. There have been attempts to implement the analysis of more than one capillary simultaneously in the electrophoresis system, but the number of capillaries has been quite small. For example, S. Takahashi et al., Proceedings of Capillary Electrophoresis Symposium, December, 1992, referred to a multi-capillary electrophoresis system in which DNA fragment samples were analyzed by laser irradiation causing fluorescence. This method, however, relies on a relatively poor focus (large focal spot) to allow coupling to only a few capillaries. Thus, this method could not be applied to a large number of capillaries. This method also results in relatively low intensity and thus poor sensitivity because of the large beam. Furthermore, detection in one capillary can be influenced by light absorption in the adjacent capillaries, thus affecting accuracy due to cross-talk between adjacent capillaries.

Attempts have been made to perform parallel DNA sequencing runs in a set of up to 24 capillaries by providing laser-excited fluorometric detection and coupling a confocal illumination geometry to a single laser beam and a single photomultiplier tube. See, for example, X. C. Huang et at., Anal. Chem., 64, 967–972 (1992), and Anal. Chem., 64, 2149–2154 (1992). Also see U.S. Pat. No. 5,274,240. However, observation is done one capillary at a time and the capillary bundle is translated across the excitation/detection region at 20 mm/see by a mechanical stage; the capillaries in this system are not transportable to a different site for measurement.

There are features inherent in the con focal excitation scheme that limit its use for very large numbers of capillaries. Because data acquisition is sequential and not truly parallel, the ultimate sequencing speed is generally determined by the observation time needed per DNA band for an adequate signal-to-noise ratio. Moveover, the use of a translational stage can become problematic for a large capillary array. Because of the need for translational movement, the amount of cycling and therefore bending of the capillaries naturally increases with the number in the array. It has been shown that bending of the capillaries can result in loss in the separation efficiency. This is attributed to distortions in the gel and multipath effects. Sensitive laser-excited fluorescence detection also requires careful alignment both in excitation and in light collection to provide for efficient coupling with the small inside diameter of the capillary and discrimination of stray light. The translational movement of the capillaries thus has to maintain stability to the order of the confocal parameter (around 25 µm) or else the cylindrical capillary walls will distort the spatially selected image due to misalignment of the capillaries in relation to the light source and photodetector. In addition, long capillaries provide slow separation, foul easily, and are difficult to replace.

U.S. Pat. No. 5,324,401 to Yeung et al. describes a multiplexer capillary electrophoresis system where excitation light is introduced through an optical fiber inserted into the capillary. In this system the capillaries remain in place, i.e. in the buffer solutions when the capillaries are read.

U.S. Pat. No. 5,332,480 (Dalton et al.) describes a multiple capillary electrophoresis device for continuous batch electrophoresis.

U.S. Pat. No. 5,277,780 (Kambara) describes a two dimensional capillary electrophoresis apparatus for use with a two dimensional array of capillaries for measuring samples, such as DNA samples, in an array of test wells.

U.S. Pat. No. 5,338,427 (Shartle et at.) describes a single use capillary cartridge having electrically conductive films as electrodes; the system does not provide for multiplexed sampling, sample handling, and electrophoresis.

U.S. Pat. Nos. 5,091,652 (Mathies et at.) and 4,675,300 (Zare et al.) describe means for detecting samples in a capillary.

U.S. Pat. No. 5,372,695 (Demorest) describes a system for delivering reagents to serve a fix capillary scanner system.

Numerous examples of sample handling for capillary electrophoresis are known. For example, James in U.S. Pat. No. 5,286,652 and Christianson in U.S. Pat. No. 5,171,531 are based on presenting a single vial of sample to a single separation capillary for a sequential series of analyses.

Goodale in U.S. Pat. No. 5,356,625 describes a device for presentation of a tray of 7 vials of sample to an array of seven capillaries for the sample injection process.

Carson in U.S. Pat. No. 5,120,414 describes injection of a sample contained within a porous membrane onto a single-capillary electrophoresis device. The end of the capillary must be in intimate contact with the porous membrane to affect sample introduction into the capillary.

In contrast, the present invention provides short disposable capillaries mounted in a frame which is integral with a liquid handling system. This system permits rapid multiplexed approach to capillary electrophoresis.

Numerous examples of multi-well devices with integral membranes are known (e.g. Mann in U.S. Pat. No. 5,043,215, Matthis in U.S. Pat. No. 4,927,604, Bowers in U.S. Pat. No. 5,108,704, Clark in U.S. Pat. No. 5,219,528). Many of these devices attach to a base unit which can be evacuated, drawing samples through the membrane for filtration.

Numerous examples of multi-channel metering devices such as multi-channel pipettes are known. One example is described in a device by Schramm in U.S. Pat. No. 4,925,629, which utilizes an eight-channel pipette to meter samples/reagents to/from multi-well plates. A second example is a 96-channel pipetting device described by Lyman in U.S. Pat. No. 4,626,509. These devices use positive displacement plungers in corresponding cylinders to draw in and expel liquid in the sampling/metering step.

Finally, Flesher in U.S. Pat. No. 5,213,766 describes a 96-channel device which contains flexible "fingers" which can be deformed out of a common plane; each "finger" can be deflected into a well of a multi-well plate to acquire a small aliquot of sample by one of several mechanisms.

The present invention differs in that it provides for simultaneously sampling of an array as samples; simultaneously handling the samples and presenting an array of the samples for capillary electrophoresis; simultaneously transferring the array of presented samples to an array of capillaries; and simultaneously conducting separations in the capillary electrophoresis columns.

SUMMARY OF THE INVENTION

The present invention encompasses methods and apparatus for simultaneously transferring samples from an array of sample holders to an array of capillary eletrophoresis columns, simultaneously conducting electrophoresis, and analyzing the capillary electrophoresis columns.

The invention encompasses a system for multiplexing capillary electrophoresis analysis of multiple samples comprising:
  a) a means for simultaneously acquiring an array of aliquots of sample from an array of samples in sample containers;
  b) a means, in combination with means (a), for simultaneously processing the array of samples to provide an array of processed samples and presenting the array of processed samples for capillary electrophoresis;
  c) means for simultaneously transferring an array of processed samples to an array of capillary electrophoresis columns;
  d) means for simultaneously conducting capillary electrophoresis on the array of the capillary electrophoresis columns from (c); and
  e) means for analyzing capillary electrophoresis columns from (d).

The invention also encompasses an electrophoresis separation plate comprising:
  a) a frame having a first and second end and having an array of electrophoresis capillaries with first and second ends mounted respectively between the first and second end of the frame;
  b) the first end of the frame having a buffer reservoir and an electrode in the buffer reservoir wherein the first end of the capillaries are in liquid communication with the buffer reservoir;
  c) the second end of the frame having a means for placing the second end of the capillaries in contact with an array of liquid samples or run buffers which is in contact with an array of electrodes and wherein there is fluid communication between the buffer reservoir and the sample or run buffer through the capillaries and electrical communication between the electrode in the buffer reservoir and the electrodes in the samples or run buffer by way of the electrophoresis capillaries.

The invention further encompasses an apparatus for processing samples from an array of sample wells comprising:
  a) a sample handling plate which defines an array of sample handling plate wells wherein each well has a sipper capillary in liquid communication with the sample handling plate well to provide an array of sipper capillaries and wherein a porous matrix is interposed between each sipper capillary and the sample handling plate well, wherein the array of sipper capillaries will simultaneously wick samples from an array of sample wells;
  b) a base plate which defines an opening to receive the sample handling plate and defines an inner chamber and means associated with the base plate and sample handling plate to seal the inner chamber and provide a sealed inner chamber;
  c) means for pressurizing and evacuating the sealed inner chamber to move liquid on either side of the porous matrix to the other side of the porous matrix.

The invention also encompasses, in another embodiment, a electrophoresis separation plate comprising a frame having a reservoir at one end and a plurality of sample sites at the other end and having an electrode at each end and a means for mounting capillary electrophoresis columns on the frame so that there is electrical communication between the electrodes and fluid communication between the sample site and reservoir when there is fluid in the sample site and reservoir. The electrophoresis plate may be transportable so that it can be moved to various locations and stored.

The invention further involves a method for multiplexed analysis of multiple samples by capillary electrophoresis comprising:

a) providing the samples in an array of sample wells;
b) simultaneously sampling the samples with a sample handling plate having an array of sample handling plate wells with sipper capillaries;
c) transferring the sample handling plate to a base plate which provides for simultaneously processing and presenting the samples for electrophoresis;
d) simultaneously transferring pressurized sample to an array of capillary electrophoresis columns;
e) simultaneously conducting separation by electrophoresis;
f) analyzing the capillary electrophoresis columns.

The electrophoresis plate comprises a frame with at least one reservoir at one end. The electrophoresis plate has a means for mounting a plurality of capillary electrophoresis columns, having first and second ends, on the frame so that there is fluid communication between the reservoir and the first end of the plurality of capillaries, when there is fluid in the reservoir, and a plurality of sample introduction sites near or at the second end of the capillaries. There is a means to make electrical connection to each end of the frame, with at least one common electrode in the reservoir in the frame at the first end of the capillaries and at least one electrode in a second common reservoir in the base plate in fluid communication with the plurality of sample sites at the second end of the capillaries. Them is a plurality of electrodes electrically connected in parallel and positioned in each of the sample introduction sites at the second end of the capillaries. This arrangement of electrodes provides for electrical communication between the electrodes at each end of the frame and the capillaries, when there is fluid in the reservoirs, capillaries and the sample introduction sites.

The invention includes methods for analyzing samples of substances which are separable by electrophoresis providing a transportable electrophoresis plate having a plurality of electrophoresis columns, simultaneously transferring sample from the multiple samples to the electrophoresis columns in the transportable plate, simultaneously conducting electrophoresis on the columns in the plate to separate the substance to be analyzed, moving the transportable plate to a location for analysis, and analyzing the substance(s) to be analyzed which are separated in the electrophoresis columns in the transportable plate. The capilllary columns may be dynamically analyzed by detecting a separated band as it moves past a stationary analysis system, or the columns may be scanned by a moveable analysis system, on imaged by an array detector.

The present invention has many advantages over conventional electrophoresis technology. For example, the confirmation of proper amplification of nucleic acids by conventional separation on gels takes hours; whereas, the system of this invention can do confirmation in about 10 minutes. Conventional gel separations are manually intensive. The invention only requires sample introduction, with the separation, detection and analysis being automatic. The invention system will perform confirmations in parallel. For example, 96 samples can be processed on a standard gel, but only with compromises in resolution and sensitivity.

The invention system can resolve a difference of 2–3 base pairs among double stranded DNA fragments of 200–300 bps. If 96 samples are run in parallel on a single standard gel, resolution for the same range of targets would be 5 to 10 fold poorer. Working with samples of unpurified PCR-amplified DNA, the present system found multiple amplified targets in several samples where the standard gel methods only detected a single band.

The present invention system typically requires only 1 to 5% of the amount of sample used on a standard gel because of the high sensitivity and hence less amplified material is required, reducing reagent cost and/or amplification time.

The capability to add a common reagent to multiple samples, mix and react means that the primary amplification step could be done on the sample handling plate, with an approximately designed thermocycler, with the benefits of amplification done in discrete small volumes, in parallel with precise timing, with a minimum of carry-over and cross contamination.

This invention has advantages with regard to quantitation of amplified nucleic acids. After amplification, the standard methods are patterned after conventional immunoassays requiring solid phase reactions (on the surface of 96-well plates or on beads), followed by washes for separation and subsequent reactions for signal generation. The whole procedure takes several hours, with many steps, and with marginal sensitivity and precision.

The present invention system can perform a quantitative determination in a much simpler format. The target is amplified with sequence specificity in the standard way; that is, for PCR, specificity is derived from the primers and for LCR specificity is derived from the ligation of adjacent hybridized probes. Then the amplified material is separated on columns and the amount of target is measured at the anticipated position on the column, based on the size of the target. That is, one quantitates the amount of target, in addition to obtaining a size-based confirmation without the need for any solid phase reactions. If additional sequence specificity is required, then an additional hybridization step could be incorporated into the procedure.

Since reactions are in the liquid phase, the invention system provides greater speed, greater specificity and less background biochemical noise and quantitation is achieved in 10's of minutes instead of hours.

The present invention system has demonstrated the detection of as little as 8 million DNA molecules (300 to 1300 bps) in the sample and therefore has high sensitivity. Because of the high sensitivity of the present system, less biological amplification is required. For example, 20 PCR cycles operating at optimum efficiency will produce 1 million molecules, starting from a single target molecule in the sample. Conventional quasi-quantitative methods typically require 30 to 40 cycles to produce enough target for reliable detection. However, the biological gain per cycle decreases as one amplifies at the higher cycle numbers (experts agree that such variability can occur at greater than about 20 cycles). This variability is a primary cause for the lack of assay precision in the conventional methods. The present invention system only requires 2 µl of sample, reducing the amount of primers, bases, enzymes, etc. required for the amplification step.

The capability to add a common reagent to multiple samples, mix and react means that the primary amplification step could be done on the sample handling plate, with an appropriately designed thermo-cycler, with the benefits of amplification done in discrete small volumes, in parallel with precise timing, with a minimum of carry-over and cross contamination.

Many of these advantages are also achieved with regard to conventional binding assays such as ELISA's. For example, quantitation can be done in 10's of minutes on 2 μl sample volumes. The capability to add a common reagent to multiple samples in, for example, a 96 well or a multi well plate, mix, and react on the sample handling plate means that a primary reaction step (e.g. displacement of a common ligand to a receptor) can be done in discrete small volumes, in parallel with precise timing, with a minimum of carryover and cross contamination, and without contamination of the starting material (e.g. any array of compound libraries).

BRIEF DESCRIPTION OF THE FIGURES

FIG. 9 shows top plan view of a preferred separation plate.

FIG. 10 shows a cross-sectional view of the preferred separation plate through a capillary.

DETAILED DESCRIPTION OF THE INVENTION

Figure 1:
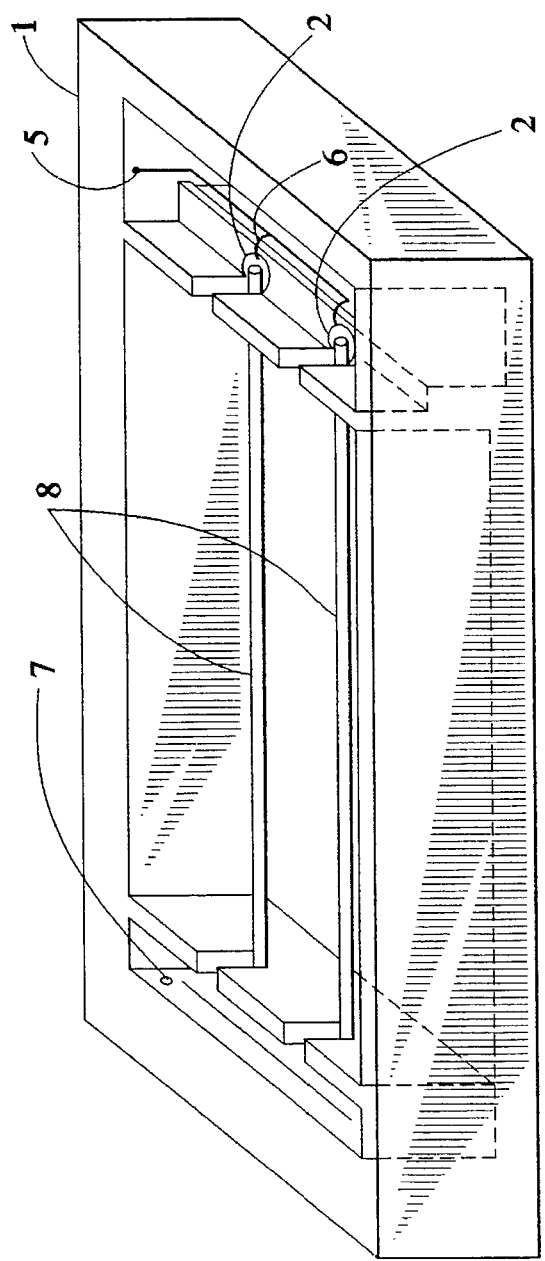
FIG. 1 is a perspective view of the electrophoresis separation plate.
Figure 2:
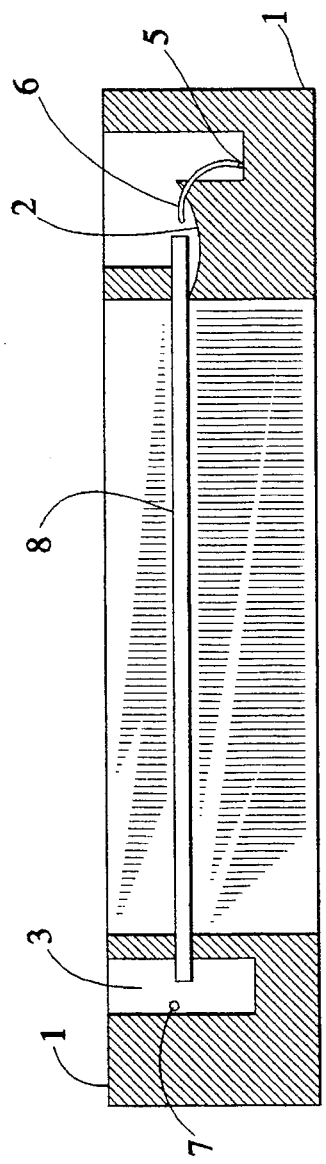
FIG. 2 is a cross-sectional view of the separation plate through a capillary.

The invention includes as shown in FIGS. 1 and 2 an elongated electrophoresis separation plate 1 which has a plurality of sample wells 2 at one end and a common buffer reservoir 3 at the other end. A first master electrode 5 is electrically connected to a cell electrode 6 in the sample wells 2. A second master electrode 7 is in the common buffer reservoir 3. Capillary electrophoresis columns 8 are mounted in the plate 1 so that there is electrical communication between the first master electrode 5 by way of the capillary electrophoresis column 8 when the sample wells 2 and the reservoir 3 are filled with electrically conductive liquid. In operation, current between the master electrodes permits electrophoresis of the sample from the sample well 2 to the reservoir 3.

Figure 3A:
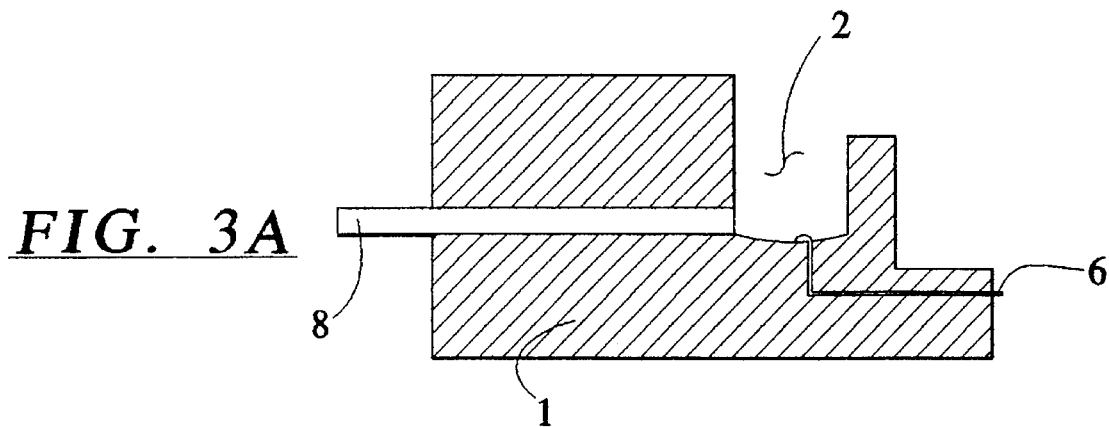
FIG. 3a shows an exploded sectional view of the well with the well electrode and capillary positioned in the well.
Figure 3B:
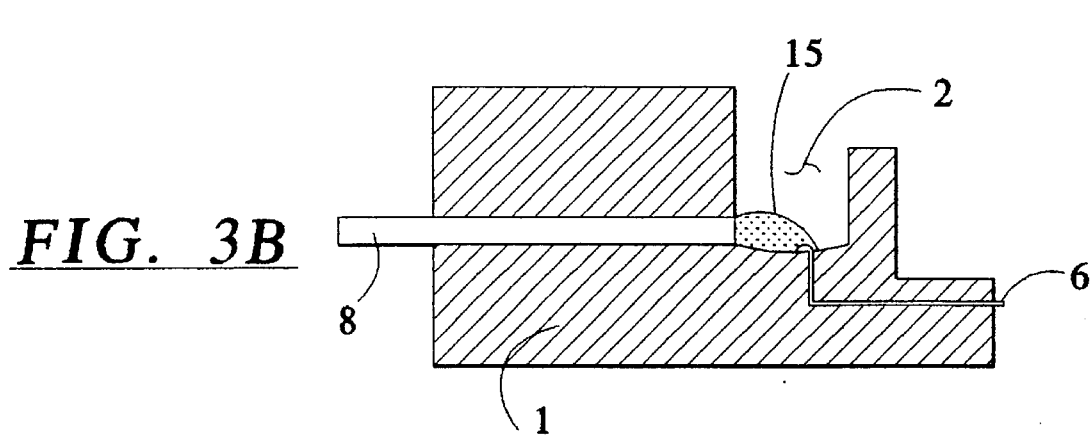
FIG. 3b shows a sample injected into the well.
Figure 3C:
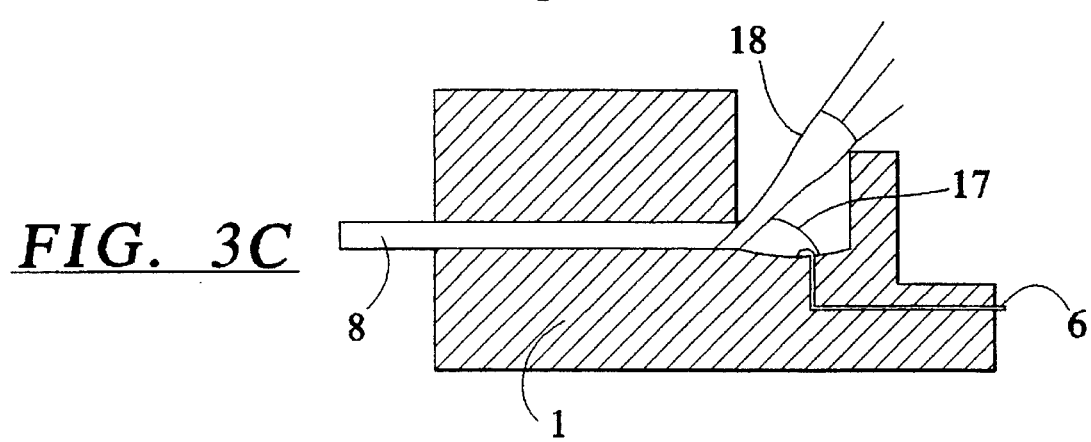
FIG. 3c shows the well with buffer and sample in the well.
Figure 3D:
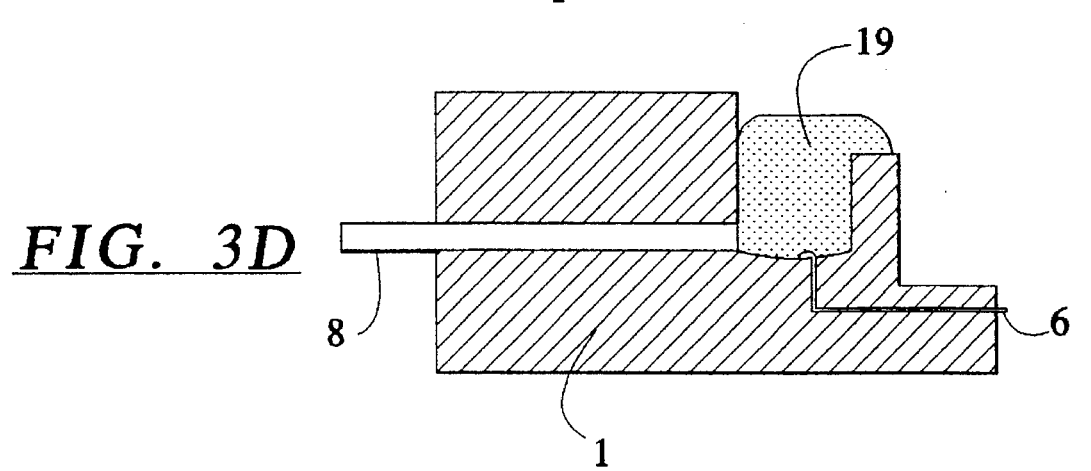
FIG. 3d shows the well when the buffer has diluted the sample.

FIG. 3a is a partial sectional view through a sample well 2 showing the well electrode 6 and capillary electrophoresis column 8. FIG. 3b illustrates the injection of a sample 15 so that there is liquid communication between the capillary 8 and cell electrode 6. The sample is loaded on the capillary via electromigration injection and then the residual sample in well 2 is diluted with buffer 19 before the electrophoresis process takes place as shown in FIG. 3d. In an alternative implementation, FIG. 3c shows a mechanical liquid transfer system where about 4 μl of buffer 17 is first added to establish liquid communication between the capillary 8 and cell electrode 6. Then 4 μl of sample 18 contained within a pipetter tip is placed in contact with the buffer 17 and sample is loaded on the column via electromigration injection. After removing the pipette tip, the well is then filled with buffer 19 as shown in FIG. 3d and the electrophoresis is conducted.

Sample may be made available for injection from the introduction site to the capillary such that only small aliquots of the primary sample are required at the introduction sites, quantitative injection is possible, and there is a minimum of carryover from one injection to another (if the plates are reused). Such sample introduction may be accomplished by a variety of means, including:

a) physically moving the capillaries relative to the introduction sites and immersing the tips of the capillaries into the respective sample aliquots positioned within the introduction sites. In this embodiment the plurality of sample introduction sites might be constructed on a separate disposable part, which moves into position for sample introduction, and then is disposed.

b) physically moving the capillaries relative to the introduction sites and bringing the tips of the capillaries to the close proximity of the sample aliquots in the introduction sites.

c) each introduction site is permanently immediately adjacent to the respective capillary tip.

Sample injection may be accomplished, simultaneously and in parallel, for the plurality of capillaries by a variety of means, including:

a) electroinjection, under the action of an electric field due to a voltage difference applied to the appropriate electrodes.

b) pressure injection, under the action of a pressure or suction applied to the fluid at one or both ends of the capillaries.

With regard to electrodes, some or all of the electrodes may be within the sample handling plate or within the electrophoresis separation plate, with external connections to power supplies, or some or all of the electrodes might be on a separate part (e.g. built into the injection and separation station), such that the electrodes can be immersed into the appropriate fluid reservoirs at the time of injection or separation. The electrodes may also be integral with the separation plate. They may be strip metal electrodes formed in a stamping process or chemical etching process. The electrodes may be wires or strips either soldered or glued with epoxy and can be made of conductive materials such as platinum, gold, copper, carbon fibers and the like. Electrodes could be integral with the sample handling plate formed by silk screening process, printing, vapor deposition, electrodeless plating process, etc. Carbon paste, conductive ink, and the like could be used to form the electrode.

Those skilled in the electrophoresis arts will recognize a large number of capillaries useful for practicing this invention. For example, fused silica is used with an outside coating of polyimide for strengthening, with inside bore ID's from 10 to 200 microns, more typically from 25 to 100 microns, and OD's greater than 200 microns. Internal coating may be used to reduce or reverse the electroosmatic flow (EOF). The simplest "coating" involves running at a low pH such that some of the silanol negative charge is neutralized. Other coatings include: silylation, polyacrylamide (vinyl-bound), methylcellulose, polyether, polyvinylpyrrolidone (PVP), and polyethylene glycol. Other materials used for capillaries include quartz, Pyrex™ and Teflon™.

Conventional buffers include the Good's buffers (HEPES, MOPS, MES, Tricine, etc.), and other organic buffers (Tris, acetate, citrate, and formate), including standard inorganic compounds (phosphate, borate, etc.). Two preferred buffered systems are:

i) 100 mM sodium phosphate, pH 7.2
ii) 89.5 mM tris-base, 89.5 mM Boric acid, 2 mM ETDA, pH 8.3. Buffer additives include: methanol, metal ions, urea, surfactants, and zwitterions interculating dyes and other labeling reagents. Polymers can be added to create a sieving buffer for the differential separation of DNA based on fragment length. Examples of polymers are: polyacrylamide (cross-linked or linear), agarose, methylcellulose and derivatives, dextrans, and polyethylene glycol. Inert polymers can be added to the separation buffer to stabilize the separation matrix against factors such as convection mixing.

Those skilled in the electrophoresis arts will recognize a wide range of useable electric field strengths, for example, fields of 10 to 1000 V/cm are used with 200–600 V/cm being more typical. The upper voltage limit for the commercial systems is 30 kV, with a capillary length of 40–60 cm, giving a maximum field of about 600 V/cm. There are reports of very high field strengths (2500–5000 V/cm) with short, small bore (10 microns) capillaries micro-machined into an insulating substrate.

Normal polarity is to have the injection end of the capillary at a positive potential. The electroosmotic flow is normally toward the cathode. Hence, with normal polarity all positive ions and many negative ions will run away from the injection end. Generally, the "end-of-capillary" detector will be near the cathode. The polarity may be reversed for strongly negative ions so that they run against the electroosmotic flow. For DNA, typically the capillary is coated to reduce EOF, and the injection end of the capillary is maintained at a negative potential.

Figure 4A:
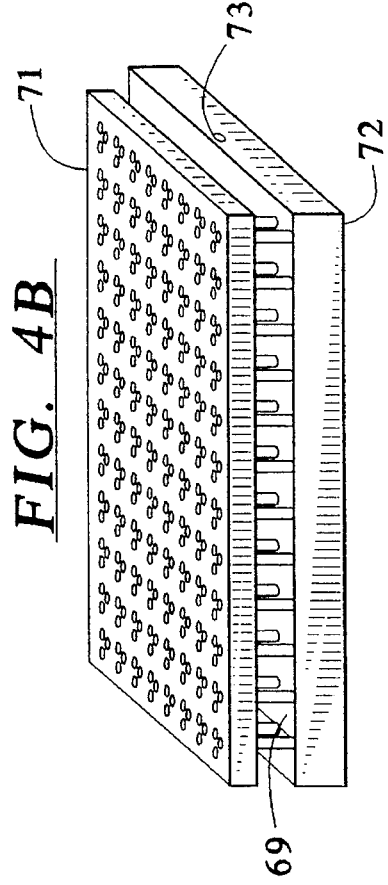
FIG. 4a–c shows a schematic of how the components of the system interact.
Figure 4B:
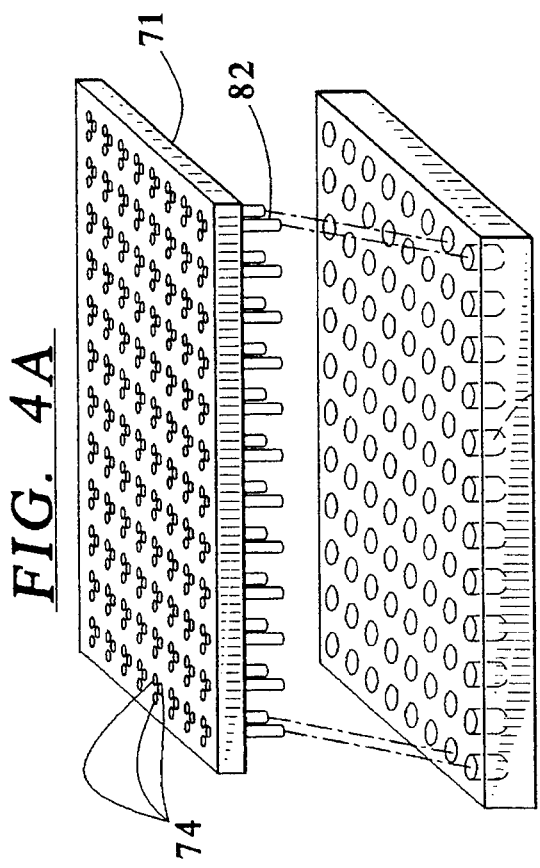
Figure 4C:
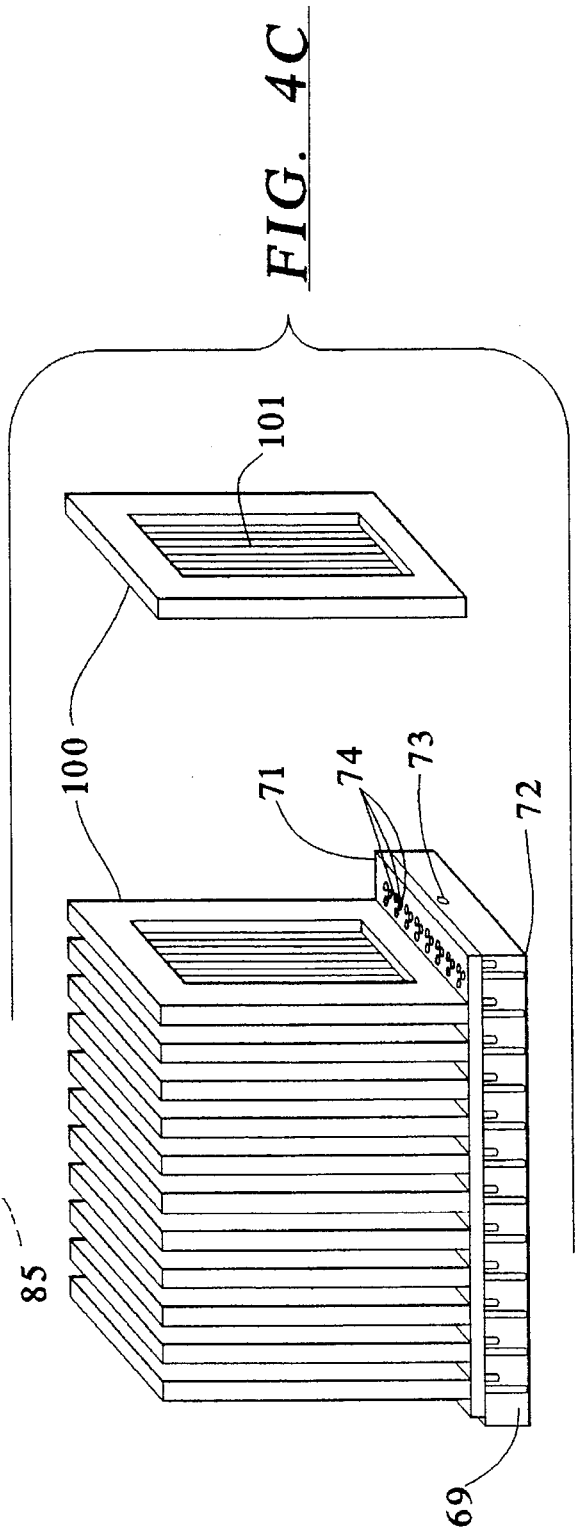

FIGS. 4a–c show the interaction of various parts of the electrophoresis system. FIG. 4a shows the sample handling plate 71 with an array of sample handling wells 74 with an corresponding array of sipper capillaries 82. The array of sipper capillaries is aligned with wells of a multiwell plate which contain samples 85. When the sipper capillaries 82 are in the sample, an aliquot of sample is transferred to the sipper capillary by wicking action. The sample handling plate 71 is then moved to base plate 72, as shown in FIG. 4b. Sample handling plate 71 and base plate 72 fit together to form a sealed inner chamber 69 which can be pressurized or evacuated through port 73. In this way, the samples in capillaries 82 can be manipulated and eventually presented in sample handling wells 74 for electrophoresis. FIG. 4c shows how the electrophoresis separation plate(s) 100 containing an array of electrophoresis capillaries 101 are aligned with the sample handling plate wells 74.

Figure 5A:
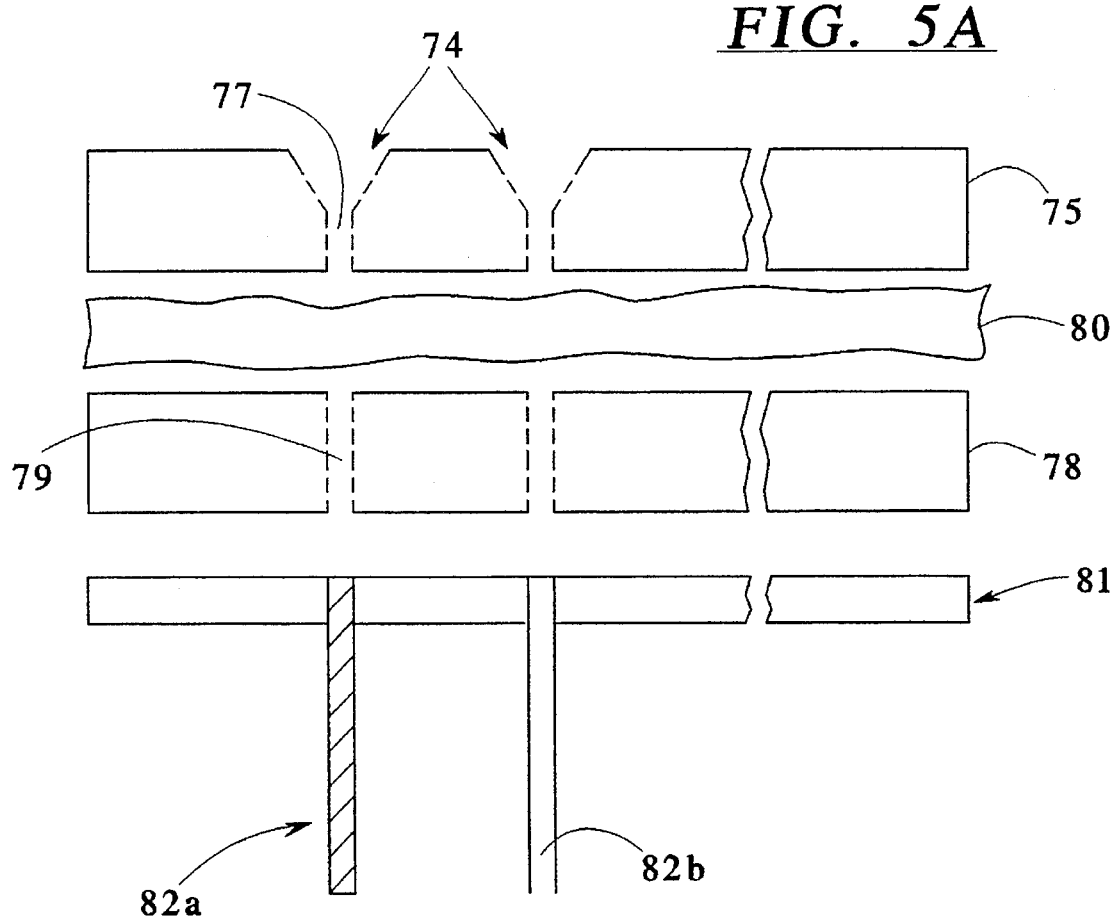
FIG. 5a shows a cross-sectional view of several sample handling plate wells.
Figure 5B:
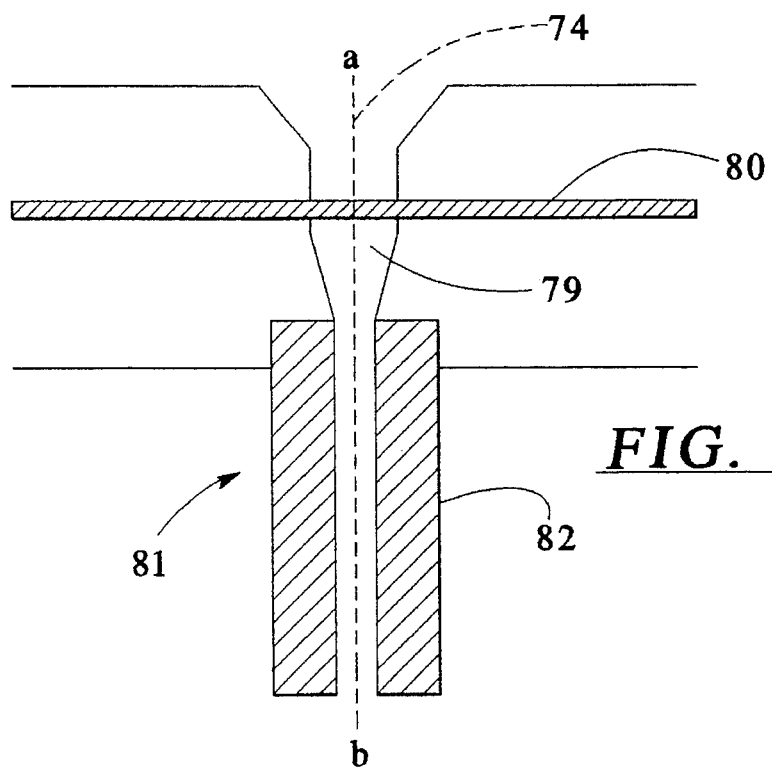
FIG. 5b shows a schematic of liquid flow from sipper capillary to sample handling plate well.

FIG. 5a shows a cross-sectional view through several wells 74. The sample handling plate 71 is assembled from a sampling block 75 which defines the funnel shaped base wells with openings 77. Mixer block 78 has passages 79 which are aligned with openings 77. The mixer block 78 and sampling block 75 are separated by a porous matrix such as membrane 80. Aligned with mixer block 78 is sipper block 81 with sipper capillaries 82. 82a is filled with sample and 82b is not. The sipper block 81, mixer-block 78, and sampling block 75 are fastened together so that a channel a–b is defined which is interrupted by the membrane 80 as shown in FIG. 5b. Membrane 80 is typically made of a wide variety of porous matrix materials where, for most applications the porous matrix materials should have little or no affinity for sample. Useful porous matrix materials include membrane materials such as regenerated cellulose, cellulose acetate, polysulfone, polyvinylidine fluoride, polycarbonate and the like. For DNA samples, a cellulose acetate membrane such as that available from Amicon is useful. For protein samples, a membrane composed of polysulfone such as those available from Amicon or Gelman is useful.

Figure 6:
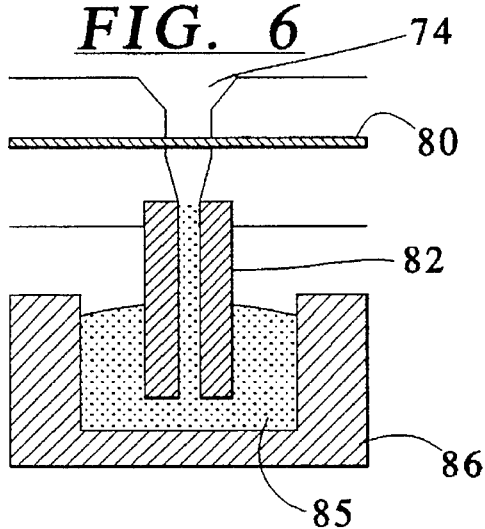
FIG. 6 shows flow of sample into sipper capillary.

FIG. 6 illustrates the flow of sample 85 from a well of a multiwell plate 86 into sipper capillary 82. Thus the ends of the array of sipping capillaries 82 on sample handling plate 71 are dipped into samples contained in an array of samples such as a 96 well plate and the samples are metered into the sipping capillaries by capillary action. At this point, the sample handling plate 71 with its sipper capillaries filled with samples is placed on base 72 to form a sealed inner chamber 69, FIG. 4b.

Figure 7A:
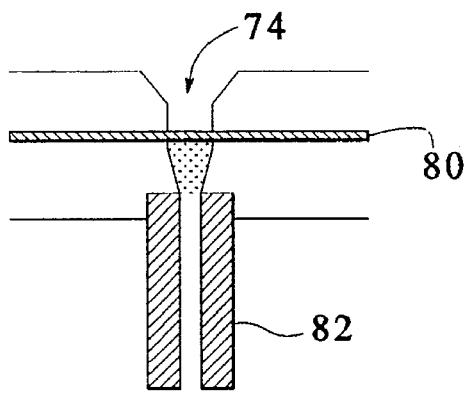
FIG. 7a–7e shows the flow of sample and reagent mixing.
Figure 7B:
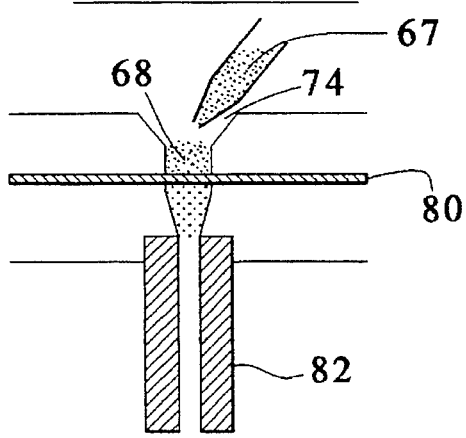
Figure 7C:
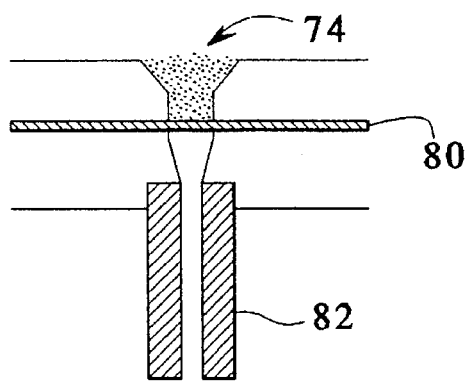
Figure 7D:
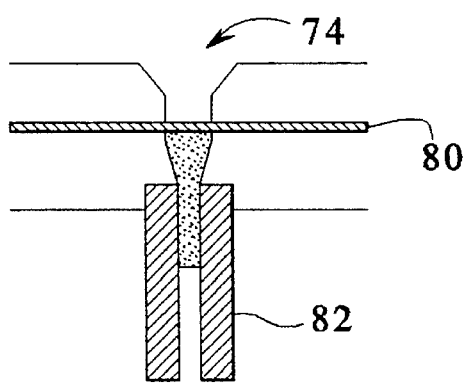
Figure 7E:
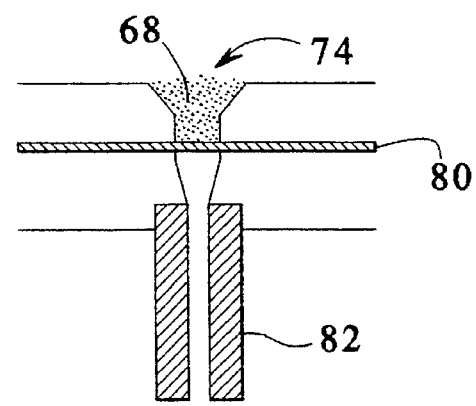

FIG. 7a–7e illustrates the flow of sample in response to pressurization and evacuation of the inner sealed chamber 69 through port 73. For example, a positive pressure moves the sample from the sipping capillary 82 to the area below the membrane, as shown in 7a, through the membrane, and into the well 74 above the membrane in plate 71. Reagents 67 can be added to the wells 74 as shown in FIG. 7b and the reagent and sample can be mixed as shown in 7c and 7d by forcing the sample and reagent back and forth through the membrane 80 in response to pressurization and evacuation of the inner sealed chamber 69. Finally, the mixed sample 68 is presented in well 74 for injection into an electrophoresis column as shown in 7e.

Figure 8:
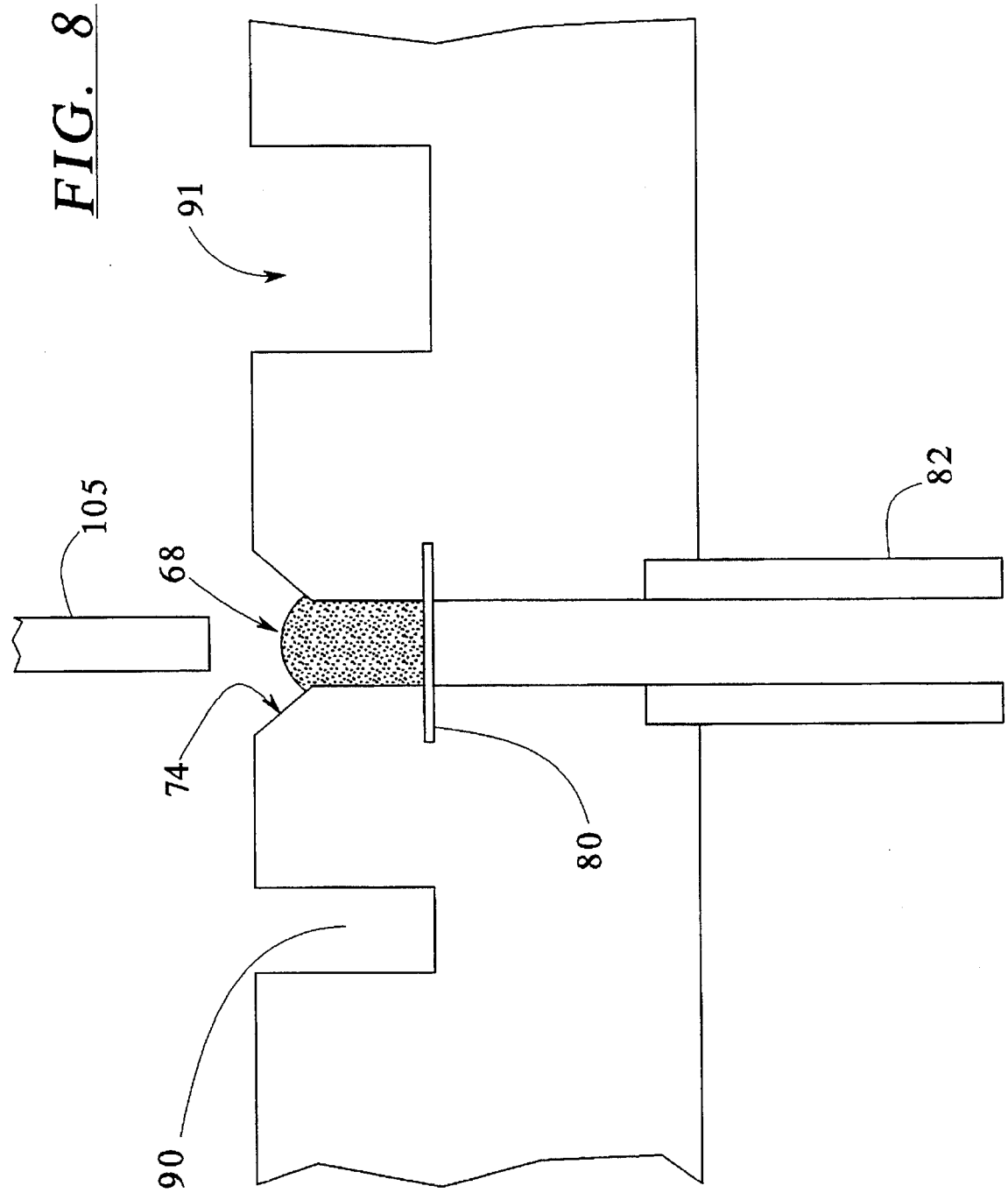
FIG. 8 shows sample handling plate with sample handling plate well and waste and primary buffer wells.

FIG. 8 illustrates the sample well 74 flanked with a well for waste electrophoresis buffer 90 from a previous separation and a well for fresh run buffer 91 which is deposited from a capillary 105 during a flushing before injecting presented sample from the sample handling well into the capillary 105 and then used during the electrophoresis separation. The capillary 105 addresses the waste 90, buffer 91 and sample 74 positions by moving the separation plate with respect to the sample handling plate for electrophoresis.

FIG. 9 shows the electrophoresis separation plate 100 having 8 capillaries 101 mounted on a frame 102; upper buffer reservoir 103 provides buffer to the capillaries 101. Orientation notch 113 provides a means for aligning the separation plate for transferring sample or reading columns. Electrode 104 and an electrode at the injection end of each of the separation capillary 105 provide for electrical communication through the buffer. FIG. 10 is a cross-sectional view through a capillary.

Those skilled in the arts will recognize that parts such as the sample handling plate, base plate and frame of the separation plate can be machined or molded from chemical resistant plastics such as polystyrene or the like.

Figure 11:
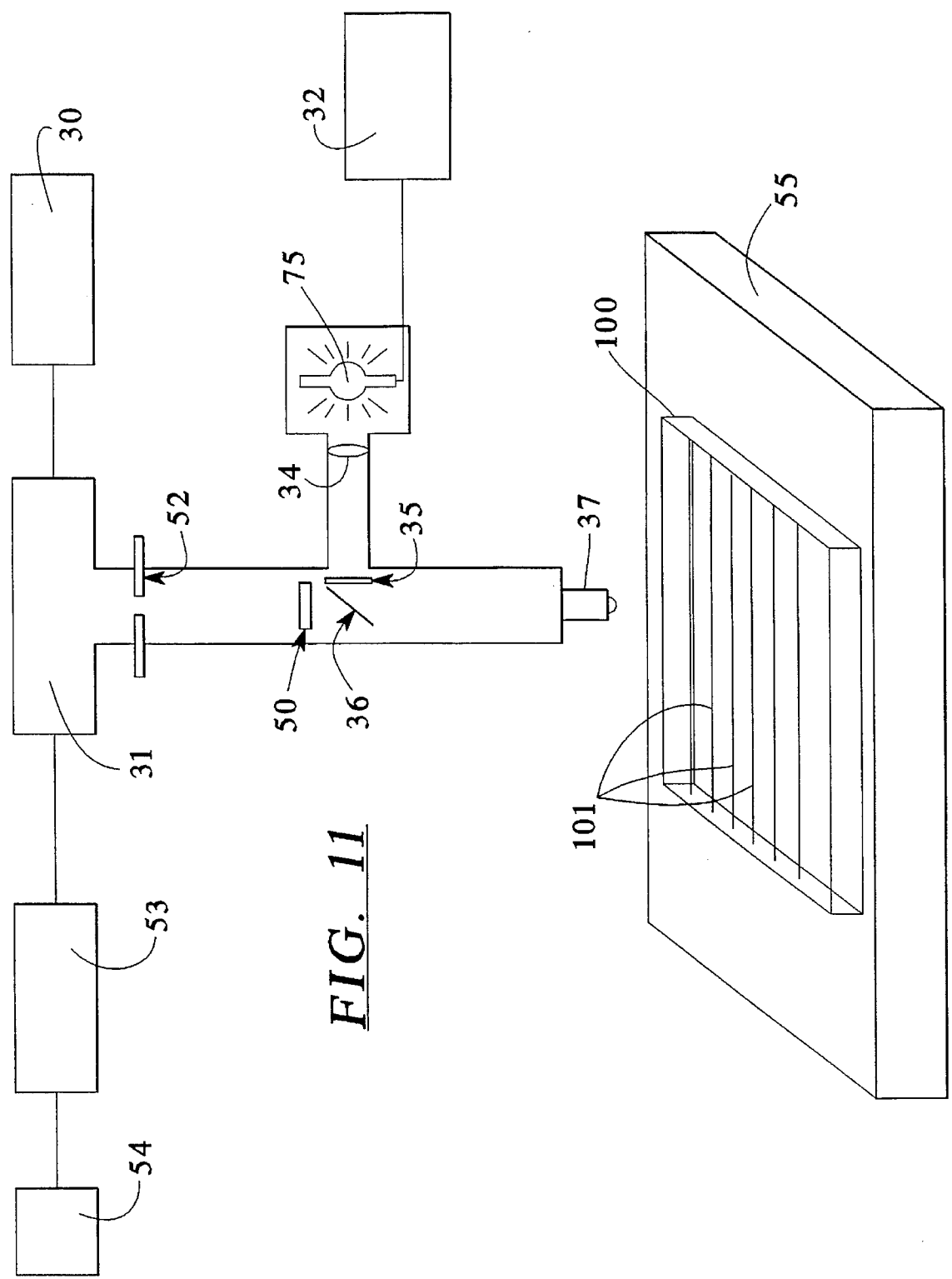
FIG. 11 shows a schematic diagram of the optical system for reading capillaries.

Thus, in operation, samples from an array of samples 85 such as a multiwell plate are wicked into an array of sipping capillaries 82 of the sample handling plate 71. The sample handling plate 71 is placed on base 72 and the sample is manipulated by pressurizing the chamber 69 defined by the sample handling and base plates and finally moved to the base plate wells 74 for presentation to the capillaries in the separation plate 100. However, prior to transferring the sample to the capillary, the capillaries are washed with buffer and primed with buffer. Samples are injected into the capillaries and electrophoresis is conducted in the capillaries in the separation plate. When the electrophoresis is finished, the separation plate may be moved to an analysis station. The over all scheme is shown in FIGS. 4a–c. After electrophoresis, the separation plate can be stored or read as shown in FIG. 11.

Capillary electrophoresis columns can be analyzed in variety of ways including the methods shown in U.S. Pat. Nos. 4,675,300, 4,274,240 and 5,324,401. The sample injection and separation are conducted in one location and the plate may be transported to a different location for analysis. FIG. 11 shows a block diagram of one optical system for reading the capillaries. Power supply 30 energizes the photomultiplier tube 31. Power supply 32 energizes a 75 watt Xenon lamp 75. Light from the lamp 75 is condensed by focusing lens 34 which passes light to the excitation filter 35. A dichroic mirror 36 directs excitation light to microscope objective 37. The separation plate 100 with capillaries 101 is mounted on a rectilinear scanner to pass the capillaries over the light from the microscope objective 37.

Those skilled in this art will recognize that the above liquid handling system provides for simultaneous and quantitative sampling of a large array of samples by sipping from the 96, 192 or 384-well plates or arrays of microtubes with an array of sipper capillaries. It provides for mixing separate aliquots in the μl range by cycling the aliquots back and forth through a porous matrix such as a membrane. The invention provides an array of addition and mixing sites for the simultaneous addition and mixing of reagents for achieving either a constant or a gradient of mixed material across the array and for precisely controlling for the simultaneous starting or stopping of reactions.

Use of activated membranes in the base plate provides for selective removal of some components of the sample of reaction mixture prior to injection. For example, an ultrafiltration membrane may be used for the removal of high molecular weight constituents or an affinity membrane, (e.g., protein-A membranes) for the removal of IgG or lectin-membranes for removal of carbohydrates or membranes with a specific antibody directed against biopharmaceutical product to remove the great excess of product for impurity analysis for process and quality control.

EXAMPLE I

This example illustrates separation and detection of MspI pBR322 fragments under the following conditions:

| | |
|---|---|
| SEPARATOR | |
| BREADBOARD: | SEPARATION PLATE AS SHOWN IN FIG. 1. |
| CAPILLARIES | |
| TYPE: | 30 MICRON ID FUSED SILICA DERIVATIZED WITH 3.5% LINEAR POLYACRYLAMIDE. |
| LENGTH: | 109 MM |
| WINDOW LOCATION: | 10–100 MM; BARE SILICA |
| CLEANING PROCEDURE | FLUSHED WITH WATER, THEN BUFFER |
| SAMPLES: | MSP I PBR 322 DNA 5 uG/ML IN 0.5 X TBE LOADED 5 IN CYLINDRICAL TEFZEL WELL FOR INJECTION |
| DETECTOR | NIKON EPI-FLUORESCENCE MICROSCOPE PTI ANALOGUE PM SYSTEM |
| GAIN: | 0.01 μA/VOLT |
| TIME CONSTANT: | 50 MSEC |
| PMT VOLTAGE: | 1000 V |
| LAMP | XENON |
| IRIS: | Open |
| N.D. FILTERS: | None |
| FILTER SET: | G2A CUBE (ETBR): (Dich 580 nm, Exc 510–560 nm, Em 590 nm) |
| FOCUS & SLITS: | focus on inner bore, set slits +25 μm on either side of bore diameter |
| DETECTOR POSITION: | 45 mm scan of capillary along x axis using detection system illustrated in FIG. 11. |
| OBJECTIVE: | 10X |
| DATA SYSTEM: | PE NELSON MODEL 1020 |
| DATA COLL. RATE: | 20–40 HZ |
| BUFFERS | |
| SAMPLE: | 0.5 X TE |
| CAPILLARY (pre load): | STOCK NUCLEOPHOR ™ BUFFER + 2.5 μg/mL ethidium bromide |
| END CHAMBERS: | At ground: ethidium bromide sieving buffer, not plugged (vented to atm pres.); at Sample end: 2.5 ug/ml ethidium bromide in TBE electrolyte |
| INJECTION | |
| METHOD: | Electrokinetic, capillary cassette in horizontal position |
| TIME: | 10 sec |
| VOLTAGE: | 3.33 kV |
| SAMPLE REMOVAL: | Removed Tefzel cylindrical well; flushed well; refilled with buffer |
| SEPARATION RUN | |
| VOLTAGE: | 3.33 kV; run for ~90 sec; capillary cassette in horizontal position |
| CURRENT: | 1.8 uA measured by hand-held multimeter |
| POLARITY: | Negative at injection end; detector near ground. |
| BUFFER: | Std Nucleophor ™ buffer + 2.5 ug/ml EtBr |
| DETECTION: | Auto scan from x = 190000 to x = 26000 via Cell Robotics Smartstage; Capillary in focus +/–5 microns across scanned length. Focus also intentionally misadjusted ½, 1, and 2 turns for scan at 500 um/sec. scans. |

Figure 12:
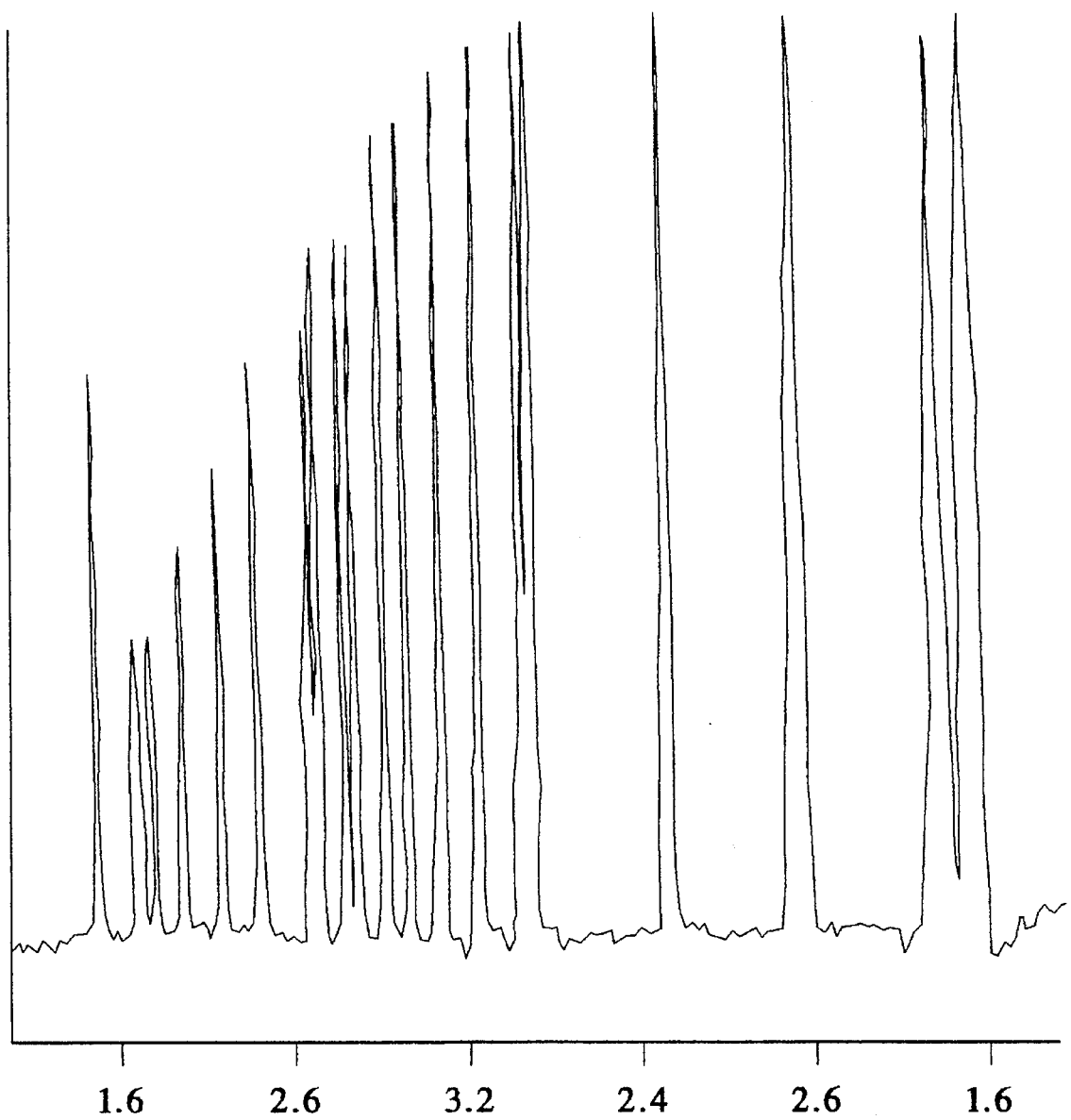
FIG. 12 graph of Msp pBR322 separation.

FIG. 12 illustrates separation of the DNA fragments.

EXAMPLE 2

This example illustrates the separation of a series of single-stranded oligonucleotides that differ by the addition of a single base to the previous oligo. The sample consists of a $pdA_{10}$ fragment which was labeled with a fluorophore (FAM) on the 5' end. The 5'FAM-pdA$_{10}$ fragments were then enzymatically extended with terminal transferase by addition of dATP onto the 3' end of the fragments. This process gave a Gaussian distribution of 5'FAM-pdA$_x$ fragments, with X ranging from ~20 to 75. Separation of this sample mimics a DNA sequencing separation in that single-stranded DNA fragments that differ by 1 base are separated and detected by fluorescence detection.

| | |
|---|---|
| Capillary: | 10 cm length μm id window at 7.5 cm, internally coated with linear polyacrylamide, positioned in separation plate illustrated in FIG. 1. |
| Buffer: | Solution of 10% $^w$/$_v$ linear polyacrylamide in 1X TBE (89 mM Tris, 89 mM borate, 2 mM EDTA) plus 7M urea loaded into the capillary via syringe. |
| Anode/Cathode Resevoir | |
| Buffer: | 1X TBE, 7M urea |
| Injection: | 10 second at 2 kV electroinjection at cathode end. |
| Separation: | 2 kV (~12 μA current) const. potential |
| Sample: | 50 nM total DNA; average of 1 nM each fragment |
| Detection: | Static; fluorescence; 470–490 nm excitation > 520 nm emission using detection scheme illustrated in FIG. 11, but with static detection. |
| Slit: | 110 μm × 20 μm, positioned 7.5 cm from injection end. |

Figure 13:
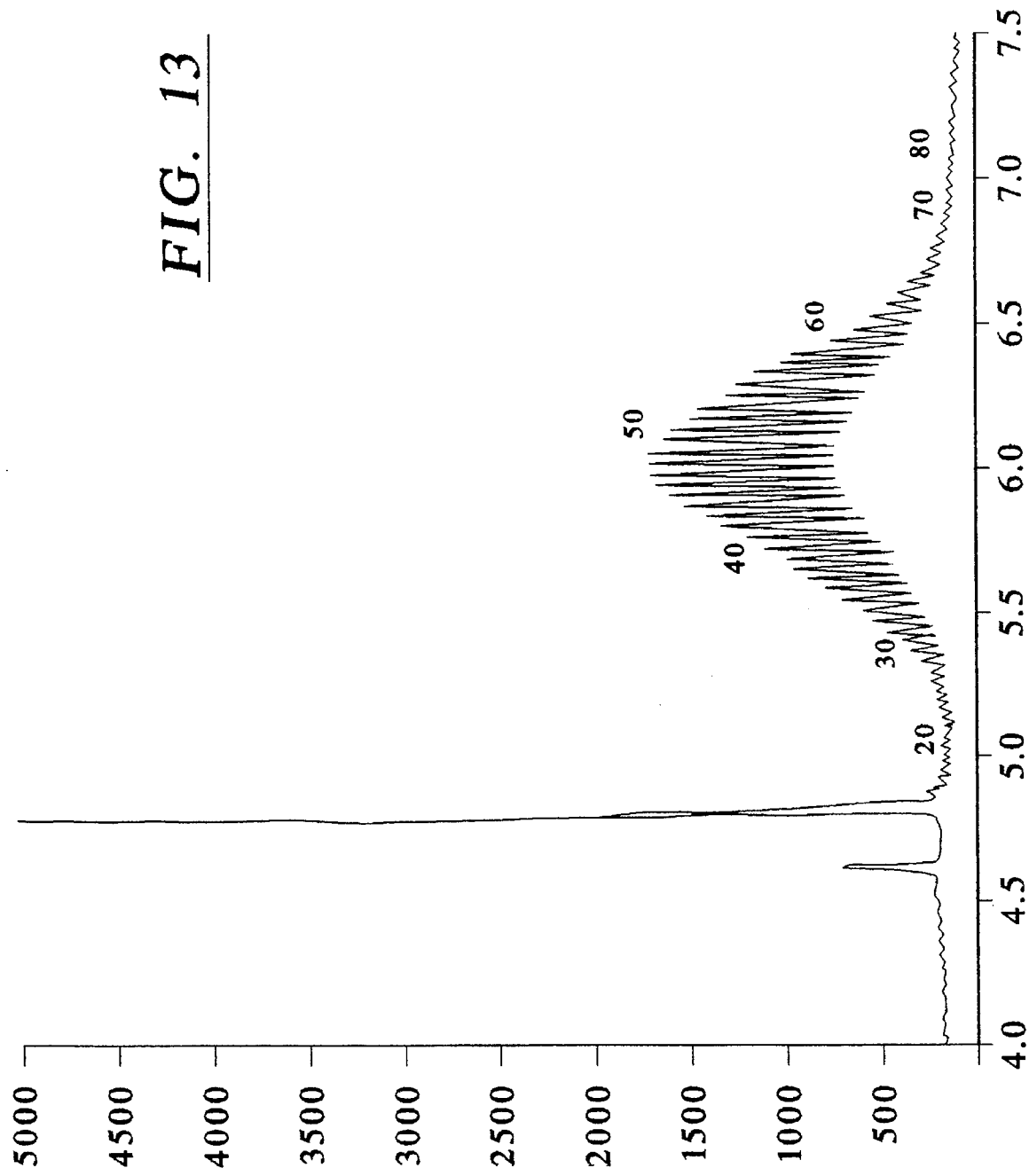
FIG. 13 shows a trace of a separation of single stranded DNA fragments differing by one base.

The results are shown in FIG. 13.

EXAMPLE 3

This example illustrates the separation of some non-standard samples of DNA. The samples were obtained by amplification of human genomic DNA samples via the PCR (polymerase chain reaction) process. Samples were not purified prior to use. Samples were diluted with a predetermined concentration of a calibration standard which contained PCR fragments of known sizes of 50, 100, 200, 300, 400, 500 . . . 1000 bp. The calibration standards were obtained from Bio-Synthesis, Inc., Louisville, Tex. Samples were diluted by 25% into the calibration standard and separated under the following conditions:

| | |
|---|---|
| Capillary: | 9.2 cm length 30 μm id 4% linear polyacrylamide coated, window at 7.0 cm from cathode end, positioned in an electrophoresis illustrated in FIG. 1. |
| Buffer: | Nucleophore ® sieving buffer. (Dionex Corp., Sunnyvale, CA) + 2.5 μg/mL ethidium bromide; loaded into capillary via syringe. |
| Cathode Buffer: | 1X TBE (89 mM Tris, 89 mM borate, 2 mM EDTA) + 2.5 μg/mL ethidium bromide. |
| Injection: | 10 sec. at 3 kV electroinjection at cathode. |
| Separation: | 3 kV constant potential. |
| Detection: | Excitation - 510–560 nm. Emission - >590 nm, using the static detection scheme illustrated in FIG. 11. |

Figure 14:
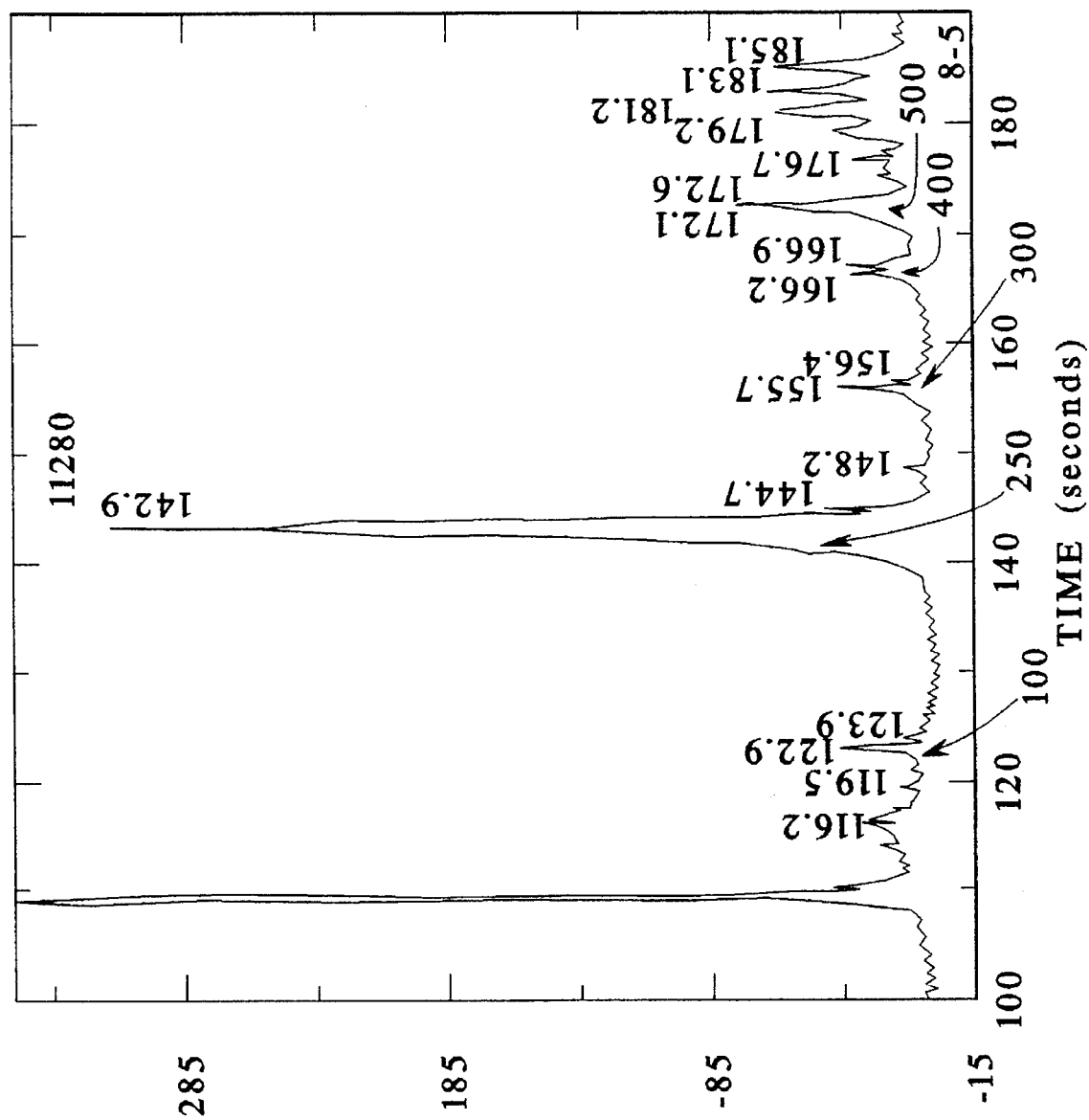
FIG. 14 shows separation of unknown DNA samples derived from PCR™ amplification.

The expected size of this DNA sample was 211 bp. The size as determined from the separation shown in FIG. 14 was 210 bp.

EXAMPLE 4

DNA Sequencing

A 96 multiple well plate with templates 1–8 to be sequenced placed in all rows of respective lanes. Primers 1–8 are in all rows of respective lanes, and all 4 bases are in all 96 positions.

The above array is sipped into the Base Plate. For sequencing, it is desirable to simultaneously sip four samples and mix those samples prior to sequencing. For example, with reactions involving four separate reactions with color coded primers, place base Plate with cover into instrument station which can control pressure within the Base Plate, control temperature, and automatically add reagents to the top of the Base Plate at the various positions.

Simultaneously add the polymerase to all 96 positions and start the pressure/vacuum cycling to mix at the membranes and to start the chain extension reaction.

With an eight-by pipetter, add fluorescently labeled, chain extension terminators (for all 4 bases, color coded), to all 8 positions of the first row. Chain extension ends in these positions, producing fragments extending from 10 (allowing for the primer) to 120 bases, for all 8 templates.

After a predetermined period of time (matched to the polymerization rate, controlled by buffer conditions), the same terminator mix is added to the second row of eight lanes. Chain extension ends in the second row, producing fragments extending from 80 to 220 bases from the starting point, for all 8 templates. The stagger and overlap of fragment sizes is determined by the time interval between terminator additions, the concentration of polymerase and bases, and the buffer conditions. The stagger of fragments may be obtained by changing the relative concentration of terminators versus bases at the various rows, or by starting all polymerization reactions simultaneously and adding an enzyme-stopper at various time points).

Additions of terminators, at predetermined time intervals is continued for all rows.

The double stranded DNA is melted and injected and then separated on the respective capillaries.

Each separation plate (at a given row) will have on-board sieving buffer optimized for the fragment size range for that row which is nominally a range of about 100 bases. Therefore reducing the relative size resolution required to obtain single base separation.

At the end of the entire process, one has simultaneously sequenced 8 templates, each for about 1200 bases, in about 30 minutes. Those skilled in this also know how to re-prime and continue the process.

The methods and apparatus of this invention have many advantages for DNA sequencing. The primary advantages of this sequencing method is that one obtains long read lengths by combining continuous (or overlapping) read windows. Hence, within each row of 8 capillaries, one needs single base resolution for a defined read window (e.g. from 490 to 610 bases). Therefore, the sieving buffer for each row of 8 capillaries, on a given electrophoresis plate, can be optimized for the particular read window.

Additional advantages are that the sequencing throughput is increased by 3 to 10 fold over current methods and that small volumes of template and reagents are required. The maine reason for the higher throughput is that separation and reading is done simultaneously for a large number of short capillaries.

Finally, though this sequencing method is ideally suited to the devices of this invention, those experienced in the art of sequencing will realize that this method may be practiced on other devices such as standard gel-based DNA separation systems.

EXAMPLE 5

Method for Protein Binding Assay of Enkephalin Analogs

Capillary: 31 μm ID fused silica, 10 cm mounted in a separation plate shown in FIG. 1. Wash at beginning and end of day with phosphate buffer and water (5 min).

Materials: Run buffer was 62.5 mM sodium phosphate, pH 8.5 with 0.01% (BSA) bovine serums albumin. Label (F-11, YGGFLTSEK(-fluorescein)SQ (TANA Labs, Houston, Tex.), competitor (YGGFLK- American Peptide Co., Sunnyvale, Calif.) and Fab' monoclonal antibody fragment (Gramsch Labs Schwabhausen Germany) were diluted in Run Buffer. Antibody and label were mixed at a concentration of 12.5 nM each; this typically added to competitor within 5 minutes after mixing. Competitor was diluted to several concentrations. Add 40 μl of Ab/label mixture to 10 μl of competitor and incubated 10 minutes before assaying. Mix by pumping action of pipet. These mixtures were stable for several hours at room temperature, if protected from evaporation and were held in the dark. Final concentrations were: 10 nM Fab', 10 nM F-11, and 0, 20, 40 or 200 nM for the competitor.

Injection: The injection area of the separation plate was rinsed with about 1 ml run buffer and all liquid removed. Using a micropipet, 4 μl of sample was delivered to the area between the capillary end and (sample well) the electrode. Sample was introduced into the capillary via electrokinetic injection for 10 seconds at 2.3 kV at the anode, at the end of which the injection area was flushed with 4 drops of run buffer to remove residual sample.

Separation: Voltage was set at 3 kV.

Detection: Laser light source; PMT; gain set at $10^{-4}$, 500 msec; detector window at 6 cm from injection. Argon ion laser, 488 nm excitation. Fluorescein was detected with a long pass filter above 520 nm.

Figures 15A, 15B:
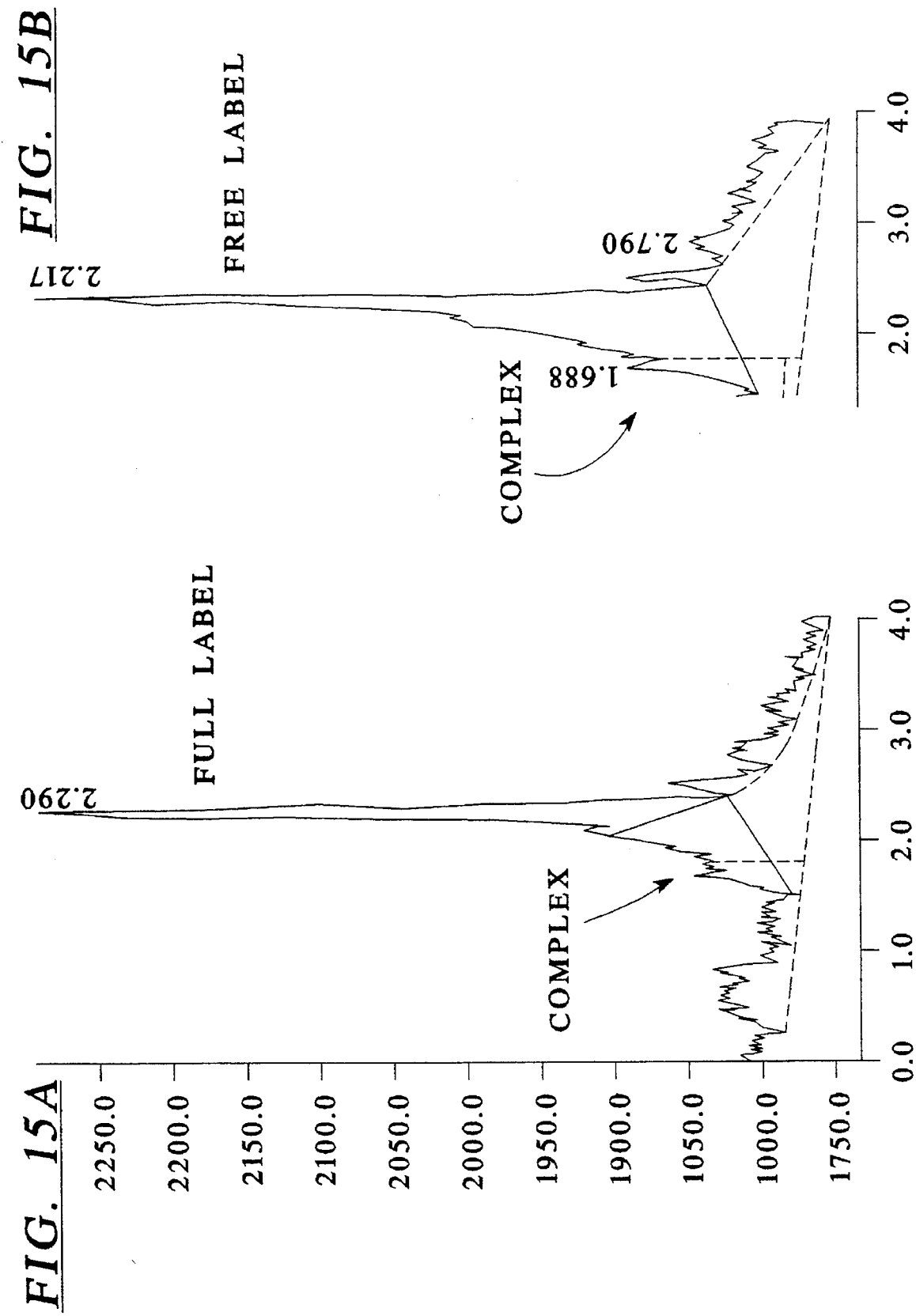
FIGS. 15A and B shows separation of a protein/binding partner complex.

Analysis: Two areas in the fluorescent electropherogram measured as shown in FIGS. 15A and B.

Area 1—under the free label peak.

Area 2—total fluoresence area, including the complex, free label, and fluorescence between the two peaks due to label coming off the Ab during migration.

Figure 16:
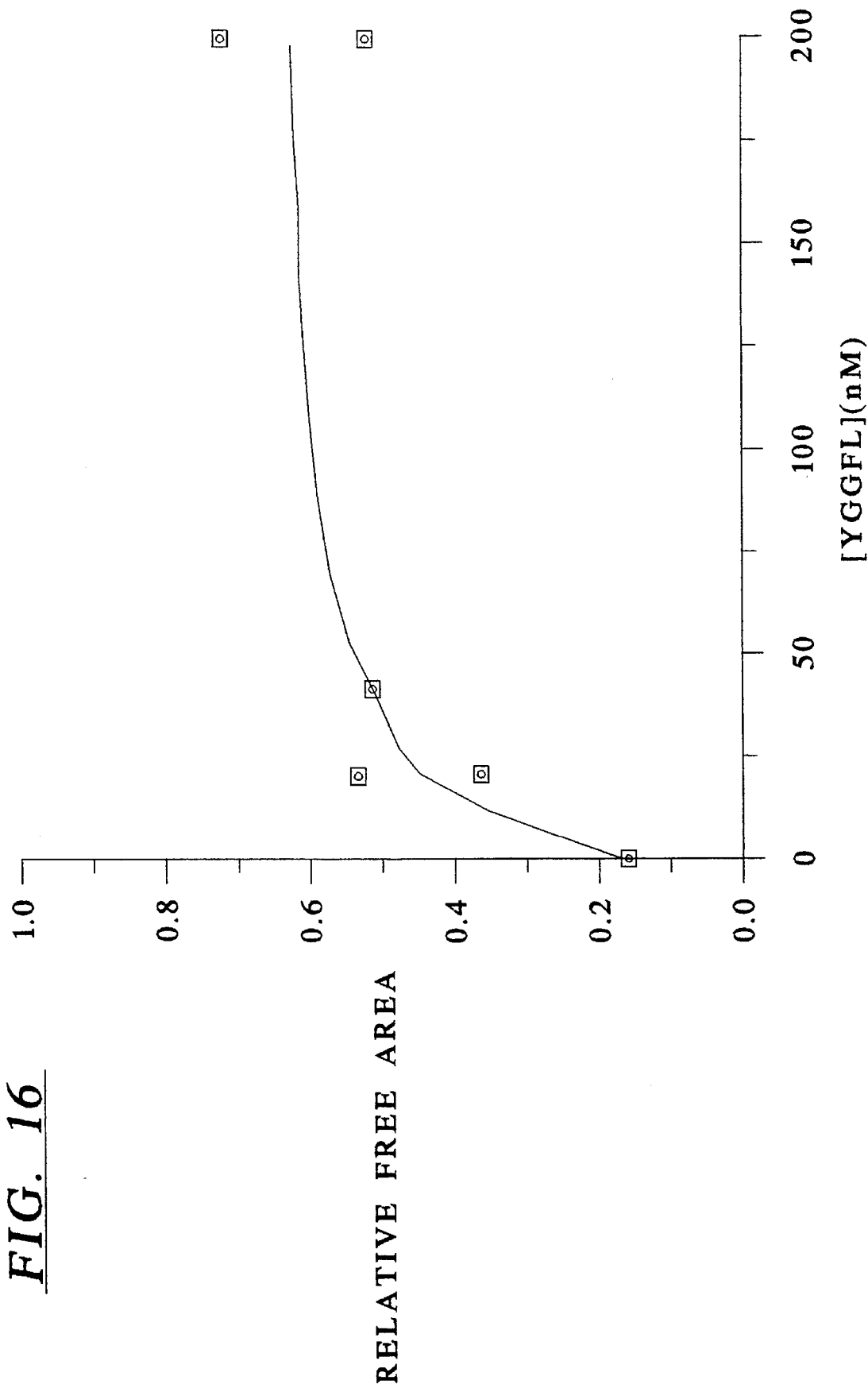
FIG. 16 shows separation of a displaced labeled peptide versus concentration of a competitor.

Area 1/Area 2 is plotted vs. [competitor] as shown in FIG. 16.

EXAMPLE 6

| Procedure for DNA Detection Limit | |
| --- | --- |
| Breadboard: | separation plate as shown in FIG. 1 |
| Capillary: | 10.1 cm of 30 μm id fused silica, covalently coated with polymeric layer of polyacrylamide; window at 6.6 cm from cathrode end, and positioned in a separation plate as illustrated in FIG. 1. |
| Anode/Capillary Buffer: | Nucleophor ™ sieving buffer (Dionex, Sunnyvale, CA) plus 2.5 μg/ml ethidium bromide. |
| Cathode buffer: | 1X TBE (89.5 mM Tris, 89.5 mM borate, 2.0 mM EDTA, pH 8.3) plus 25 μg/ml ethidium bromide. |
| Detector: | as illustrated in FIG. 13, run in the static detection mode. excitation 510–560 nm emission > 590 nm |
| Injection Run: | 30 sec at 3.0 kV @ cathode 3.0 kV constant voltage |

| Procedure for DNA Detection Limit | |
| --- | --- |
| Sample: | 0.033 μg/ml Hae III digest of ØX 17 4 DNA (Sigma Chemical Co., St. Louis, MO) in water |

Figure 17:
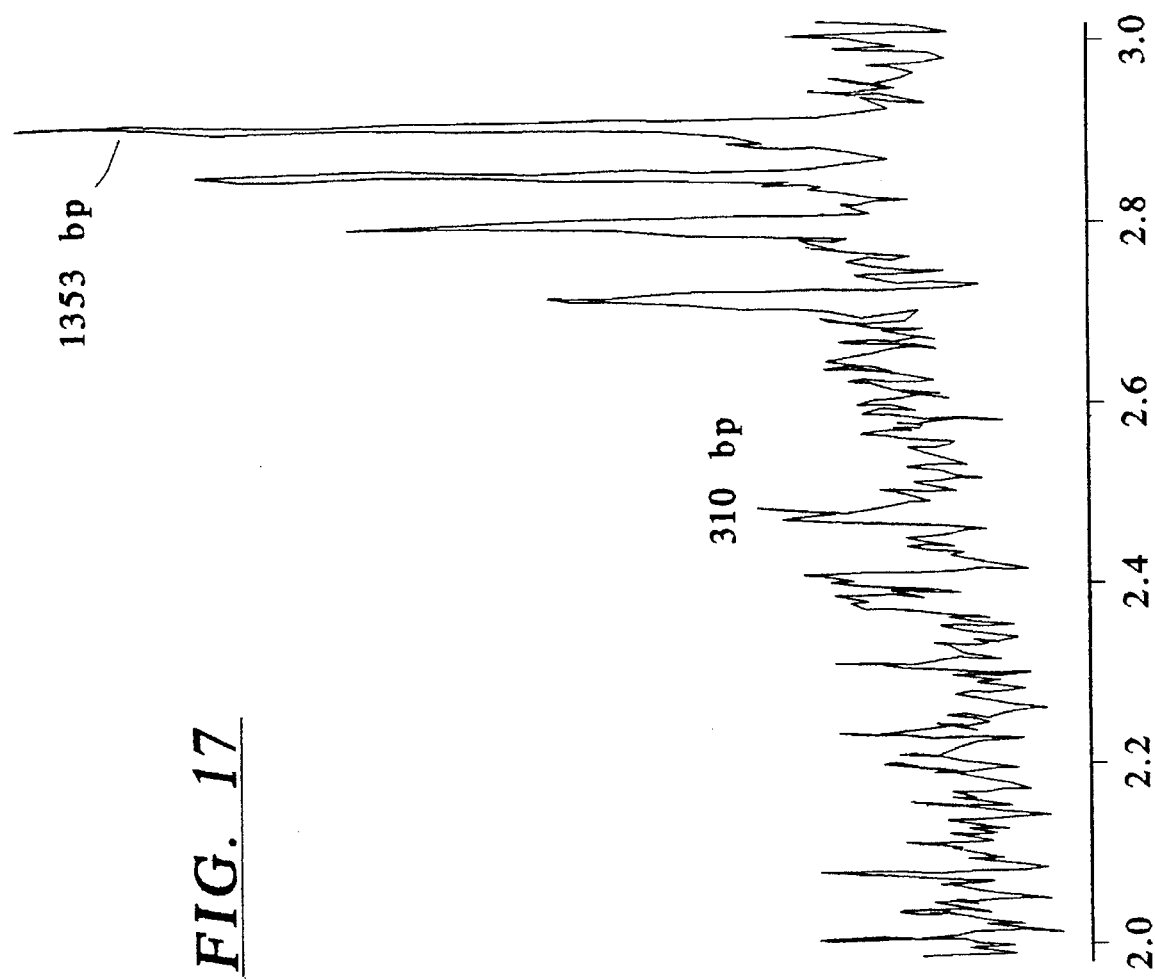
FIG. 17 illustrates the limits of detection of DNA.

FIG. 17 shows that 12 picogram or 14 attomoles of 1353 bp DNA can be detected and that 2–3 picograms or 14 attomoles of 310 bp DNA can be detected.

EXAMPLE 7

Figure 18:
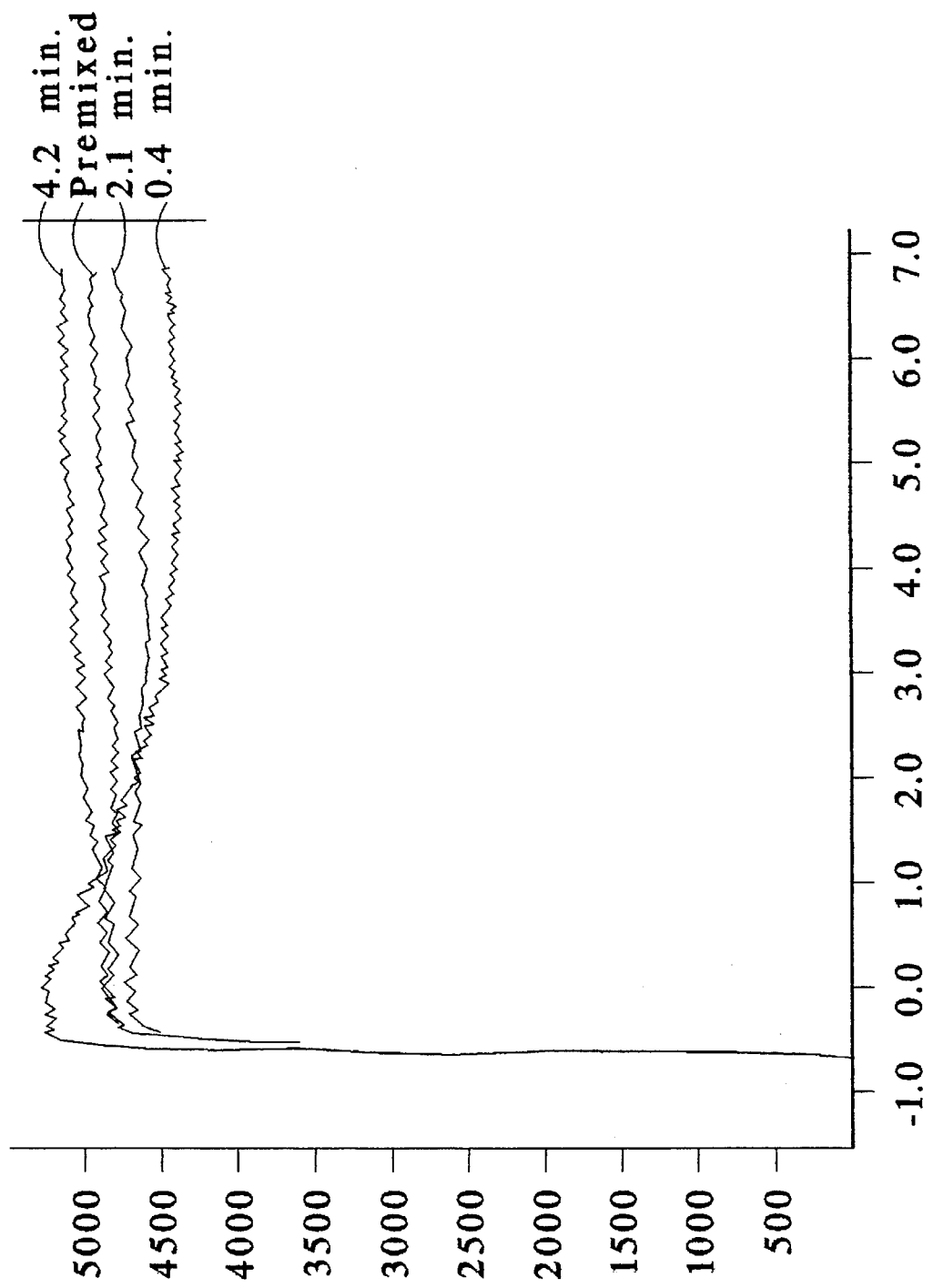
FIG. 18 shows the efficiency of mixing of two samples in the sample handling plate.
Figure 19A:
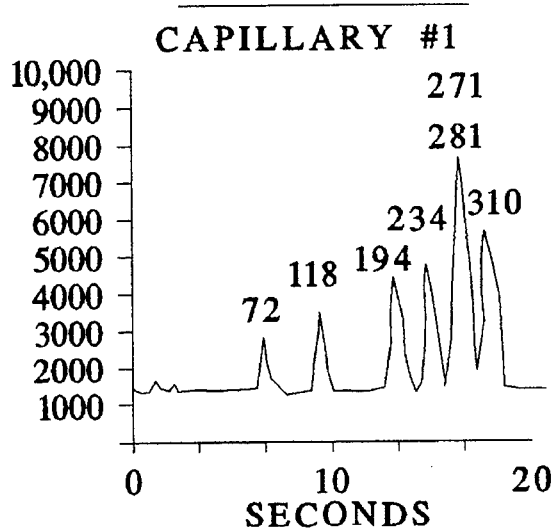
FIGS. 19A–F illustrates the reproduceability of simultaneous sipping, sample handling, electrophoresis and then analysis of DNA samples.
Figure 19B:
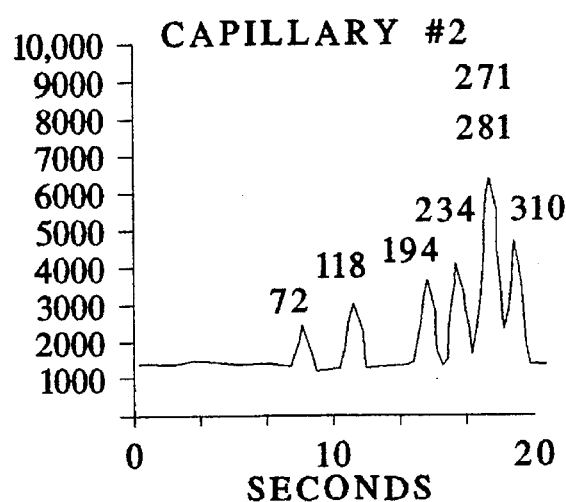
Figure 19C:
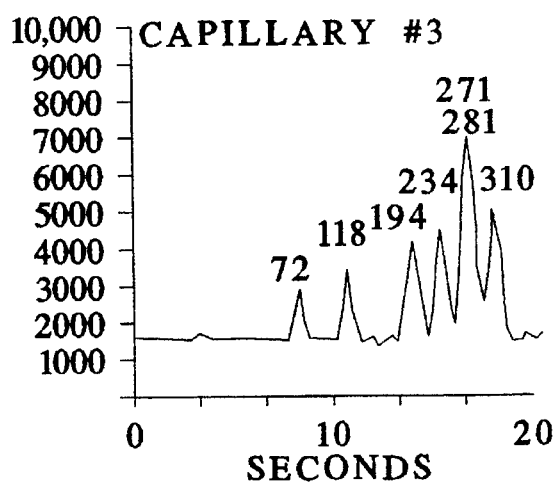
Figure 19D:
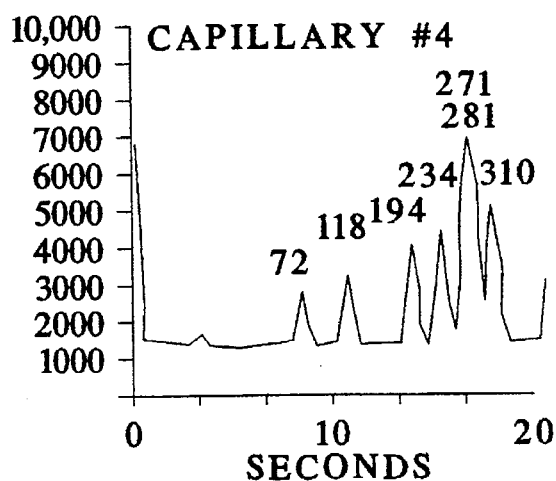
Figure 19E:
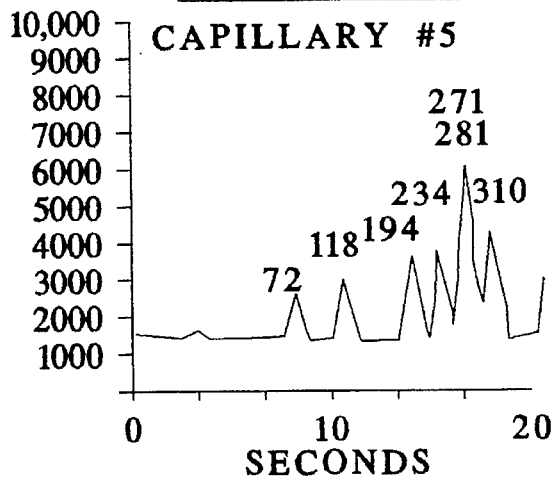
Figure 19F:
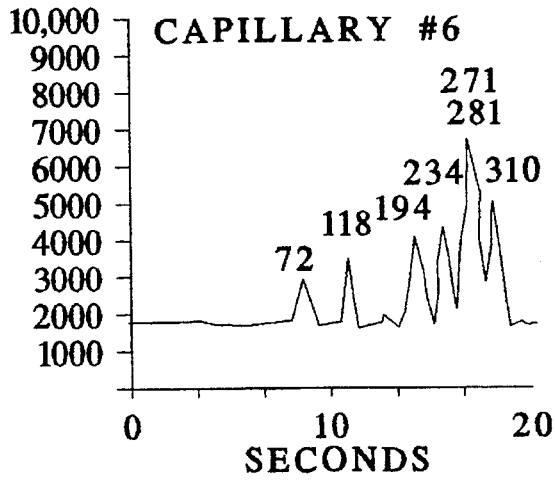

FIG. 18 illustrates the efficiency of mixing very small volumes of reagents as described in FIGS. 7a–e. Thus, 1.9 μl of a dye (xylene cyanole) was mixed with 1.9 μl of water and the mixed sample was passed back and forth through the membrane 80 for 0.4, 2.1 or 4.2 minutes.

The above examples are intended to illustrate the present invention and not to limit it in spirit and scope.

EXAMPLE 8

This example demonstrates a combined sample sipping, sample presentation, sample injection, separation, and scanning detection of separated sample components.

| Sipper/Mixer | |
| --- | --- |
| Sipper: | 2.5 cm lengths of 538 micron id fused silica capillary in a polycarbonate plate |
| Mixing Block: | 764 micron × 16 mm peek channels in polycarbonate block |
| Top Plate: | polycarbonate |
| Membrane: | 0.45 Micron pore membrane |
| Volume | 7.30 microliters from array of PCR tubes, |
| Speed: | each with 30 microliters sample |
| Separator | |
| Breadboard: | Plate as shown in FIG. 9 |
| Capillaries | |
| Type: | 100 micron id fused silica derivatized with 4% linear polyacrylamide coating |
| Length: | 109 mm |
| Window Location: | 90 mm Total: +/–45 mm from center point of capillaries |
| Cleaning Procedure: | Flushed with water, then sieving buffer solution from syringe |
| Samples: | HAE III digest of pBR 322 DNA from Sigma Chemical Co. 10 microgram/ml in 0.5% TE buffer 30 microliters of sample were loaded into each of 6 PCR tubes as primary sample array sample array |
| Detector | |
| Optical | |
| Lamp: | 75 watt Xenon |
| Iris: | 1/8 opened |
| N.D. Filters: | ND1 and ND2 out |
| Gain: | 0.1 microamp/volt |
| Time Constant: | 50 Milliseconds |
| PMT Voltage: | 850 volts |
| Filter Set: | G2A cube (ETBR):(Dichroic 580 nm, Exc. 510–560 nm, EM. 590 nm) |
| Focus & Slits: | Focus on inner bore of capillary; Slits 150 × 20 microns centered over inner bore |
| Objective: | 10x |
| Scanner: | Cell robotics smartstage scanner |
| Scan Speed: | 1760 Microns/Sec |
| X Scan | X - 33000 TX x - .36000 microns |

-continued

Range:
Buffers

| | |
|---|---|
| Sample: | 0.5X TE (5 mM TRIS, pH 7.5, 1 mM EDTA) |
| Capillary: | Stock nucleophor buffer (Dionex Corporation) + 2.5 microgram/ml ethidium bromide |
| Common Resevoir: | Stock nucleophor buffer (Dionex Corporation) + 2.5 microgram/ml ethidium bromide |
| Array Resevoirs: | 1 × TBE (89.5 mM tris base, 89.5 mM boric acid, 2 mM EDTA, pH 8.3) + 2.5 microgram/ml ethidium bromide |
| Power Supply: | Bertan, modified with timer/controller |
| Polarity: | Negative |

Injection

| | |
|---|---|
| Method: | Electrokinetic, from sampling plate on horizontal |
| Duration: | 15 seconds |
| Voltage: | 3.3 kV |
| Sample Removal: | Moved electrophoresis plate to transfer capillaries from sample wells to run buffer wells |

Separation Run

| | |
|---|---|
| Voltage: | 3.3 kV |
| Duration: | 120 seconds |
| Current: | 156 microamps total for the 6 capillaries |
| Detection: | sequential scan of the 6 individual capillaries at 1770 microns per second |
| Data System: | PE/Nelson Model 1020 |
| Input: | 10 Volts fulls scale |
| Sampling Rate: | 20 Hertz |

This simultaneously sipping an array of six samples, simultaneously presenting the samples through the sample handling block, simultaneously electroinjecting the presented samples into the capillaries, simultaneously conducting the electrophoresis following by analysis is demonstrated. FIGS. 19A–F illustrates the separation and reproductability of separation of the system for DNA sequences having a size between 72 and 310 base pairs.

What is claimed is:

1. An electrophoresis separation plate comprising:

a) a transportable frame having first and second ends and having an array of electrophoresis capillaries with first and second ends mounted respectively between the first and second ends of the frame;

b) the first end of the frame having a buffer reservoir and an electrode in the buffer reservoir wherein the first end of the capillaries are in liquid communication with the buffer reservoir; and c) the second end of the frame having a means for placing the second end of the capillaries in contact with an array of liquid samples or run buffer which is in contact with electrodes and wherein there is fluid communication between the buffer reservoir and the array of samples or the run buffer through the electrophoresis capillaries and electrical communication between the electrode in the buffer reservoir and the electrodes in the samples or run buffer by way of the electrophoresis capillaries.

2. A system for capillary electrophoresis analysis of an array of samples in an array of sample containers comprising:

a) means for simultaneously transferring at least a portion of each sample in the array of samples to a corresponding array of capillary electrophoresis columns wherein the capillary electrophoresis columns are in the electrophoresis plate of claim 1;

b) means for simultaneously conducting capillary electrophoresis separations on the array of transferred samples in the capillary electrophoresis columns; and c) means for analyzing capillary electrophoresis separations from (b).

3. An apparatus for processing an array of samples from an array of sample wells comprising:

a) a sample handling plate which defines an array of sample handling plate wells wherein each well has a sipper capillary in liquid communication with the sample handling plate well to provide an array of sipper capillaries and wherein a porous matrix is interposed between each sipper capillary and each sample handling plate well, wherein the array of sipper capillaries will simultaneously wick an array of samples from an array of sample wells;

b) a base plate which defines an opening to receive the sample handling plate and defines an inner chamber to means associated with the base plate and sample handling plate to seal the inner chamber and provide a sealed inner chamber; and c) means for pressurizing and evacuating the sealed inner chamber to move liquid on either side of the porous matrix to the other side of the porous matrix.

4. Electrophoresis separation plate comprising:

a frame having a buffer reservoir at one end and a plurality of sample sites at the other end and having an electrode at each end, a means for mounting capillary electrophoresis columns on the frame so that there is electrical communication between the electrodes and fluid communication between the sample sites and reservoir when there is fluid in the sample sites, capillary electrophoresis columns and buffer reservoir.

5. A method for analysis of an array of samples in an array of sample containers by capillary electrophoresis comprising:

a) providing an array of samples in an array of sample wells;

b) simultaneously transferring at least a portion of each sample in the array of sample wells to a corresponding array of capillary electrophoresis columns wherein the capillary electrophoresis columns are in the electrophoresis separation plate of claim 1;

c) simultaneously conducting separation of the transferred samples by capillary electrophoresis; and d) analyzing the capillary electrophoresis separations of (c).

6. A method for analysis of an array of samples in an array of sample containers by capillary electrophoresis comprising:

a) providing the array of samples in an array of sample wells;

b) simultaneously acquiring an aliquot of each sample from the array of samples with a sample handling plate having an array of sample handling plate wells with sipper capillaries;

c) transferring the sample handling plate to a base plate which provides for simultaneously processing and then presenting the samples for capillary electrophoresis;

d) simultaneously transferring at least a portion of the presented samples to an array of capillary electrophoresis columns;

e) simultaneously conducting separations by capillary electrophoresis of the presented transferred samples; and f) analyzing the capillary electrophoresis separation of e.

7. A system according to claim 2 wherein the array of samples conforms to the format of a 96, 192 or 384 well plate.

8. A separation plate according to claim 1 wherein the plate contains 8, 12, 16 and 24 electrophoresis capillaries spaced apart to match the spacing in a row or columns of 8, 12, 16 or 24 wells in a 96, 192, or 384 well plate.

9. The apparatus of claim 3 wherein the sipper capillaries of the sample handling plate wells are in an array which conforms to a format of a 96, 192 or 384 well plate.

10. The apparatus of claim 3 wherein the means for pressurizing and evacuating is programmed to alternately pressurize and evacuate the inner chamber to mix reagents added above the porous matrix with sample below the porous matrix.

11. The method of claim 5 wherein the array of samples is nucleic acid of varying length.

12. The method of claim 5 wherein the array of samples is a specifically binding protein, its binding partner or the complex of the two.

13. The method of claim 6 wherein one or more reagents are added to the sample handling plate wells and mixed with the samples.

14. The method of claim 6 wherein the array of electrophoresis columns are rinsed for reuse to separate additional samples.

15. The electrophoresis separation plate of claim 1 wherein there is provided adjacent to sample handling plate wells a buffer wash well and a run buffer well.

16. The electrophoresis separation plate of claim 1 wherein electrodes are mounted in the frame near the second end of the capillaries so that when the capillaries are in the samples or the run buffer there is electrical communication between the electrode in the buffer reservoir and the electrodes near the capillaries.

17. The apparatus of claim 3 wherein the porous matrix is a membrane.

\* \* \* \* \*